United States Patent
Kreek et al.

(10) Patent No.: US 11,091,497 B2
(45) Date of Patent: Aug. 17, 2021

(54) PYRANO[3,4-B]PYRAZINE KAPPA OPIOID RECEPTOR LIGANDS FOR TREATING ADDICTION, PRURITUS, PAIN, AND INFLAMMATION

(71) Applicant: The Rockefeller University, New York, NY (US)

(72) Inventors: Mary Jeanne Kreek, New York, NY (US); Amy Ripka, Reading, MA (US); Brian Reed, New York, NY (US); Eduardo Butelman, New York, NY (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 16/769,858

(22) PCT Filed: Dec. 7, 2018

(86) PCT No.: PCT/US2018/064422
§ 371 (c)(1),
(2) Date: Jun. 4, 2020

(87) PCT Pub. No.: WO2019/113419
PCT Pub. Date: Jun. 13, 2019

(65) Prior Publication Data
US 2021/0179629 A1    Jun. 17, 2021

Related U.S. Application Data

(60) Provisional application No. 62/596,357, filed on Dec. 8, 2017.

(51) Int. Cl.
*C07D 491/052* (2006.01)

(52) U.S. Cl.
CPC .................. *C07D 491/052* (2013.01)

(58) Field of Classification Search
CPC combination set(s) only.
See application file for complete search history.

(56) References Cited

U.S. PATENT DOCUMENTS

| | | | |
|---|---|---|---|
| 4,816,465 A * | 3/1989 | Clemence ............ | C07D 401/06 514/314 |
| 8,211,908 B2 | 7/2012 | Kiyoto et al. | |
| 8,778,958 B2 | 7/2014 | Cashman | |
| 10,118,896 B2 | 11/2018 | Aube et al. | |
| 2010/0311761 A1* | 12/2010 | Wunsch ............... | A61P 1/04 514/249 |
| 2013/0150340 A1 | 6/2013 | Plettenburg et al. | |
| 2015/0133432 A1 | 5/2015 | Hachtel et al. | |
| 2016/0122307 A1* | 5/2016 | Abels ................... | C07D 241/42 514/161 |

FOREIGN PATENT DOCUMENTS

| | | | | |
|---|---|---|---|---|
| WO | 1997049422 A1 | 12/1997 | | |
| WO | WO-2014184356 A1 * | 11/2014 | ........... | C07D 241/42 |
| WO | WO-2016079109 A1 * | 5/2016 | ........... | C07D 241/38 |
| WO | 2019113419 A1 | 6/2019 | | |
| WO | WO-2020247599 A1 * | 12/2020 | ......... | C07D 491/052 |

OTHER PUBLICATIONS

Abdel-Jalil; Tetrahedron Letters 1998, 39, 7703-7704. DOI: 10.1016/S0040-4039(98)01677-3 (Year: 1998).*
Bourgeois; Bioorg Med Chem 2014, 22, 3316-3324. doi: 10.1016/j.bmc.2014.04.054. (Year: 2014).*
Galla; Med. Chem. Commun. 2016, 7, 317-326. DOI: 10.1039/c5md00414d (Year: 2016).*
Halfpenny; J Med Chem. 1989, 32, 1620-1626. doi: 10.1021/jm00127a036 (Year: 1989).*
Helal; European Journal of Medicinal Chemistry 2017, 141, 632-647. DOI: 10.1016/j.ejmech.2017.10.012 (Year: 2017).*
Molenveld; Bioorg Med Chem Lett 2015, 25, 5326-5330. doi: 10.1016/j.bmcl.2015.09.040. (Year: 2015).*
Schenk; Psychopharmacology 1999, 144, 339-346. DOI: 10.1007/s002130051016 (Year: 1999).*
Soeberdt; J. Med. Chem. 2017, 60, 6, 2526-2551. DOI: 10.1021/acs.jmedchem.6b01868 (Year: 2017).*
Wenker; Med. Chem. Commun. 2016, 7, 2368-2380. DOI: 10.1039/c6md00441e (Year: 2016).*
International Search Report and Written Opinion issued in PCT/US2018/64422, dated Feb. 7, 2019.
Dunn et al. Signaling Properties of Structurally Diverse Kappa Opioid Receptor Ligands: Toward in Vitro Models of in Vivo Responses, ACS Chemical Neuroscience, vol. 10, No. 8, Jul. 17, 2019, [retrieved on Aug. 9, 2020]. Retrieved 'from the Internet. <URL: https://pubs.acs.org/doi/abs/10.1021 /acschemneuro.9b00195>, abstract, Jul. 17, 2019.

* cited by examiner

Primary Examiner — Daniel R Carcanague
(74) Attorney, Agent, or Firm — Heslin Rothenberg Farley & Mesiti, P.C.; Philip Hansen

(57) ABSTRACT

1-Phenylacetyl-8-aminohexahydro-2H-pyrano[3,4-b]pyrazines of formula

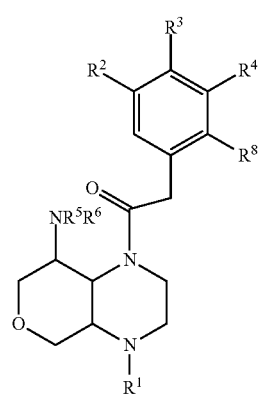

are disclosed. The compounds are kappa ligands and are useful to treat drug dependency, pruritus, pain, and inflammation.

20 Claims, No Drawings

PYRANO[3,4-B]PYRAZINE KAPPA OPIOID RECEPTOR LIGANDS FOR TREATING ADDICTION, PRURITUS, PAIN, AND INFLAMMATION

CROSS-REFERENCE TO RELATED APPLICATIONS

This application is a U.S. National Phase filing under 35 U.S.C. § 371 of International Application PCT/US2018/064422, filed Dec. 7, 2018, and published as WO2019/113419 A1 on Jun. 13, 2019. PCT/US2018/064422 claims priority from U.S. provisional application 62/596,357, filed Dec. 8, 2017. Both are incorporated herein by reference in their entirety.

FIELD OF THE INVENTION

The invention relates to kappa opioid receptor ligands of the 1-phenylacetyl-8-aminohexahydro-2H-pyrano[3,4-b]pyrazine family that are useful to treat disorders such as drug dependency, pruritus, pain, inflammation, and mood disorders.

BACKGROUND OF THE INVENTION

One-and-a-half million current (past-month) cocaine users (12 or older) (approximately 0.6% of the U.S. population) were reported in 2014. The 2011 Drug Abuse Warning Network (DAWN) report showed that, of the nearly 1.3 million visits to emergency departments for illicit drug misuse or abuse, cocaine was involved in over 500,000 of these emergency department visits. No medication has been shown to be effective in humans for treating cocaine dependence.

Exposure to cocaine, which inhibits the biogenic amine neurotransmitter transporters, acutely causes increased extracellular dopamine, serotonin, and norepinephrine, and also results in changes in components of the endogenous opioid system. Acutely, cocaine results in increased gene expression of dynorphin in the dorsal and ventral striatum, in animal models. Chronic cocaine exposure also results in changes in mu and kappa opioid receptor binding. Similar alterations have been detected in human postmortem brain following cocaine abuse or dependence. Kappa opioid receptor/dynorphin dysfunction has been observed following experimental stress in animals, with accompanying depressant-like behavioral effects. Additionally, PET imaging has shown brain KOP-r populations to be altered in people exhibiting symptoms of trauma, including anhedonia or dysphoria and anxiety.

Full kappa agonists have the ability to block the rewarding effects of cocaine, but by themselves they have been shown to be aversive [see Zhang et al. *Psychopharmacology* 179(3): 551-558 (2005)]. Similarly, dysphoria and psychotomimetic/hallucinogenic effects result from KOP-r agonist administration in humans [see Pfeiffer et al. *Science* 233 (4765): 774-776 (1986)]. Kappa antagonists have been shown to block stress induced reinstatement to cocaine seeking in animal self-administration models, but with no effect on drug-induced reinstatement.

Although multiple selective KOP-r antagonists (with no agonistic efficacy, and full blockade) have been identified to date, no selective partial or differentially efficacious G-protein/beta-arrestin signaling biased KOP-r agonists have been previously reported to be tested in animal models of drug addiction.

Chronic pruritus, which is defined as itch persisting for more than 6 weeks, has a number of causes and is associated with a markedly reduced quality of life. Chronic pruritus is characteristic of several dermatologic diseases (e.g., atopic eczema, psoriasis, lichen planus, and scabies) but also occurs in a variety of noncutaneous disorders. The causes of chronic pruritus can be broadly categorized into four major groups: dermatologic causes, systemic causes (e.g., cholestasis, chronic kidney disease, myeloproliferative disorders, and hyperthyroidism), neuropathic causes (e.g., notalgia paresthetica [a distinctive itch of the upper back] and brachioradial pruritus [a characteristic itch of the arms, probably caused by spinal-nerve impingement]), and psychogenic causes. Kappa agonists such as nalfurafine (TRK-820) have been shown to abolish the chloroquine-induced scratching in murine models [see Inan and Cowan *Eur J Pharmacol.*, 502, 233-237 (2004)]. Thus, KOP-r agonists are expected to be useful for the treatment of chronic pruritus.

Kappa agonists exert potent analgesic activity in a wide variety of visceral pain models. These effects are mediated at peripherally located κ-receptors and possibly through additional nonopioid action at sodium channels located on peripheral nerve endings of primary sensory afferents. The analgesic potency of κ-agonists in visceral pain is enhanced in the presence of inflammation. Thus, KOP-r agonists are expected to be useful for the treatment of pain and inflammation.

Recent research suggests that kappa full agonists are potentially useful for mania, and kappa partial agonists may find use for mood stabilization. However, currently available agents have some unfavorable properties. The development of kappa-selective agonists with improved drug-like characteristics may provide mood-modulating medications.

SUMMARY OF THE INVENTION

It has now been found that 1-phenylacetyl-8-aminohexahydro-2H-pyrano[3,4-b]pyrazine derivatives are KOP-r ligands with differential agonistic activity, making them useful to treat dependence on cocaine as well as other psychostimulants and alcohol. They are also useful to treat pruritus, pain, inflammation, and mood disorders.

In one aspect, the invention relates to compounds of Formula I

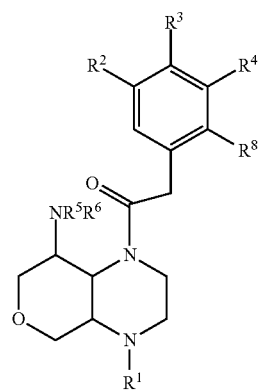

wherein $R^1$ is chosen from hydrogen, $(C_1-C_{10})$hydrocarbyl, $-C(=O)(C_1-C_{10})$hydrocarbyl, $-C(=O)O(C_1-C_{10})$hydrocarbyl and $-SO_2(C_1-C_{10})$hydrocarbyl;

$R^2$, $R^3$, $R^4$, and $R^8$ are chosen independently from hydrogen, halogen, $(C_1-C_4)$alkyl, fluoro$(C_1-C_4)$alkyl, nitro, —SO$_3$H and —N$^+$HR$^5$R$^6$; with the provisos that (1) at least one of $R^2$, $R^3$, $R^4$, and $R^8$ must be other than hydrogen; and (2) when $R^2$ or $R^4$ is fluorine, at least one of the remaining substituents on phenyl must be other than hydrogen; and $R^5$ and $R^6$ are chosen from $(C_1-C_{10})$hydrocarbyl, optionally substituted with fluoro; or, taken together with the nitrogen to which they are attached, $R^5$ and $R^6$ form a five-, six- or seven-membered non-aromatic heterocycle, which may be optionally substituted with fluoro or $(C_1-C_4)$alkyl.

In another aspect, the invention relates to a method for activating a kappa opioid receptor. The method comprises contacting a kappa opioid receptor with a compound as described herein.

In another aspect, the invention relates to a method for treating addiction, particularly cocaine addiction. The method comprises administering to a patient a compound as described herein.

In another aspect, the invention relates to a method for treating mood disorders. The method comprises administering to a patient a compound as described herein.

In another aspect, the invention relates to a method for treating pruritus. The method comprises administering to a patient a compound as described herein.

In another aspect, the invention relates to a method for treating pain. The method comprises administering to a patient a compound as described herein.

In another aspect, the invention relates to a method for treating inflammation. The method comprises administering to a patient a compound as described herein.

In another aspect, the invention relates to pharmaceutical compositions comprising a pharmaceutically acceptable carrier and a compound as described herein.

DETAILED DESCRIPTION OF THE INVENTION

In one aspect, the invention relates to compounds of formula I

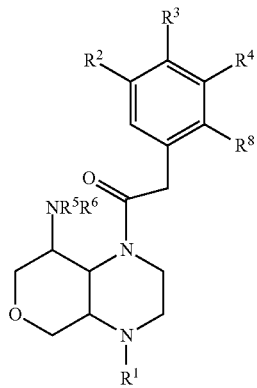

I

In some embodiments, $R^1$ is hydrogen. In some embodiments, $R^1$ is $(C_1-C_{10})$hydrocarbyl. In some embodiments, $R^1$ is $(C_1-C_7)$hydrocarbyl. In some embodiments, $R^1$ is $(C_5-C_7)$ hydrocarbyl. In some embodiments, $R^1$ is $(C_1-C_7)$alkyl. In some embodiments, $R^1$ is benzyl. In some embodiments, $R^1$ is $(C_3-C_4)$alkyl. In some embodiments, $R^1$ is methyl. In some embodiments, $R^1$ is —CH$_2$R$^{10}$, wherein $R^{10}$ is $(C_4-C_6)$carbocycle.

In some embodiments, $R^1$ is —C(=O)$(C_1-C_{10})$hydrocarbyl. In some embodiments, $R^1$ is —C(=O)O$(C_1-C_{10})$hydrocarbyl. In some embodiments, $R^1$ is —C(=O)O$(C_1-C_3)$ hydrocarbyl. In some embodiments, $R^1$ is —SO$_2$$(C_1-C_{10})$ hydrocarbyl. In some embodiments, $R^1$ is —SO$_2$$(C_1-C_8)$ hydrocarbyl. In some embodiments, $R^1$ is —SO$_2$$(C_1-C_3)$ alkyl.

In some embodiments, $R^2$ is hydrogen. In some embodiments, $R^2$ is halogen. In some embodiments, $R^2$ is $(C_1-C_4)$ alkyl. In some embodiments, $R^2$ is fluoro$(C_1-C_4)$alkyl. In some embodiments, $R^2$ is nitro. In some embodiments, $R^2$ is —SO$_3$H. In some embodiments, $R^2$ is —N$^+$HR$^5$R$^6$. In some embodiments, $R^2$ is $(C_1-C_3)$alkyl. In some embodiments, $R^2$ is chloro. In some embodiments, $R^2$ is fluoro. In some embodiments, $R^2$ is trifluoromethyl. In some embodiments, $R^2$ is methyl. In some embodiments, $R^2$ is fluoro$(C_1-C_3)$ alkyl.

In some embodiments, $R^3$ is hydrogen. In some embodiments, $R^3$ is halogen. In some embodiments, $R^3$ is $(C_1-C_4)$ alkyl. In some embodiments, $R^3$ is fluoro$(C_1-C_4)$alkyl. In some embodiments, $R^3$ is nitro. In some embodiments, $R^3$ is —SO$_3$H. In some embodiments, $R^3$ is —N$^+$HR$^5$R$^6$. In some embodiments, $R^3$ is $(C_1-C_3)$alkyl. In some embodiments, $R^3$ is chloro. In some embodiments, $R^3$ is fluoro. In some embodiments, $R^3$ is trifluoromethyl. In some embodiments, $R^3$ is methyl. In some embodiments, $R^3$ is fluoro$(C_1-C_3)$ alkyl.

In some embodiments, $R^4$ is hydrogen. In some embodiments, $R^4$ is halogen. In some embodiments, $R^4$ is $(C_1-C_4)$ alkyl. In some embodiments, $R^4$ is fluoro$(C_1-C_4)$alkyl. In some embodiments, $R^4$ is nitro. In some embodiments, $R^4$ is —SO$_3$H. In some embodiments, $R^4$ is —N$^+$HR$^5$R$^6$. In some embodiments, $R^4$ is $(C_1-C_3)$alkyl. In some embodiments, $R^4$ is chloro. In some embodiments, $R^4$ is fluoro. In some embodiments, $R^4$ is trifluoromethyl. In some embodiments, $R^4$ is methyl. In some embodiments, $R^4$ is fluoro$(C_1-C_3)$ alkyl.

In some embodiments, $R^5$ is $(C_1-C_{10})$hydrocarbyl. In some embodiments, $R^5$ is fluoro$(C_1-C_{10})$hydrocarbyl. In some embodiments, $R^5$ is $(C_1-C_6)$hydrocarbyl. In some embodiments, $R^5$ is methyl.

In some embodiments, $R^6$ is $(C_1-C_{10})$hydrocarbyl. In some embodiments, $R^6$ is fluoro$(C_1-C_{10})$hydrocarbyl. In some embodiments, $R^6$ is $(C_1-C_6)$hydrocarbyl. In some embodiments, $R^6$ is methyl. In some embodiments, $R^6$ is cyclopropylmethyl.

In some embodiments, $R^5$ and $R^6$, taken together with the nitrogen to which they are attached, form a five-membered non-aromatic heterocycle. In some embodiments, $R^5$ and $R^6$, taken together with the nitrogen to which they are attached, form a six-membered non-aromatic heterocycle. In some embodiments, $R^5$ and $R^6$, taken together with the nitrogen to which they are attached, form a seven-membered non-aromatic heterocycle.

In some embodiments, $R^5$ and $R^6$, taken together with the nitrogen to which they are attached, form a five-membered non-aromatic heterocycle, which is substituted with fluoro. In some embodiments, $R^5$ and $R^6$, taken together with the nitrogen to which they are attached, form a six-membered non-aromatic heterocycle, which is substituted with fluoro. In some embodiments, $R^5$ and $R^6$, taken together with the nitrogen to which they are attached, form a seven-membered non-aromatic heterocycle, which is substituted with fluoro.

In some embodiments, $R^5$ and $R^6$, taken together with the nitrogen to which they are attached, form a five-membered non-aromatic heterocycle, which is substituted with $(C_1-C_4)$ alkyl. In some embodiments, $R^5$ and $R^6$, taken together with the nitrogen to which they are attached, form a six-membered non-aromatic heterocycle, which is substituted with $(C_1$-$C_4)$alkyl. In some embodiments, $R^5$ and $R^6$, taken together with the nitrogen to which they are attached, form a seven-membered non-aromatic heterocycle, which is substituted with $(C_1$-$C_4)$alkyl.

In some embodiments, $R^5$ and $R^6$, taken together with the nitrogen to which they are attached, form a five-membered non-aromatic heterocycle, which may be substituted with fluoro or $(C_1$-$C_4)$alkyl. In some embodiments, $R^5$ and $R^6$, taken together with the nitrogen to which they are attached, form a six-membered non-aromatic heterocycle, which is substituted with fluoro and $(C_1$-$C_4)$alkyl. In some embodiments, $R^5$ and $R^6$, taken together with the nitrogen to which they are attached, form a seven-membered non-aromatic heterocycle, which is substituted with fluoro and $(C_1$-$C_4)$alkyl.

In some embodiments, $R^5$ and $R^6$, taken together with the nitrogen to which they are attached, form a pyrrolidine ring.

In some embodiments, —$NR^5R^6$ is

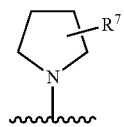

and $R^7$ is hydrogen; in others $R^7$ is fluoro. And in others $R^7$ is $(C_1$-$C_3)$alkyl.

In some embodiments, $R^8$ is hydrogen. In some embodiments, $R^8$ is halogen. In some embodiments, $R^8$ is $(C_1$-$C_4)$alkyl. In some embodiments, $R^8$ is fluoro$(C_1$-$C_4)$alkyl. In some embodiments, $R^8$ is nitro. In some embodiments, $R^8$ is —$SO_3H$. In some embodiments, $R^8$ is —$N^+HR^5R^6$.

In summary, the invention relates to:

[1]. A compound of formula I.
[2]. A compound according to [1] above wherein $R^1$ is hydrogen.
[3]. A compound according to [1] above wherein $R^1$ is $(C_1$-$C_{10})$hydrocarbyl.
[4]. A compound according to [1] above wherein $R^1$ is $(C_1$-$C_7)$hydrocarbyl.
[5]. A compound according to [1] above wherein $R^1$ is $(C_5$-$C_7)$hydrocarbyl.
[6]. A compound according to [1] above wherein $R^1$ is $(C_1$-$C_7)$alkyl.
[7]. A compound according to [1] above wherein $R^1$ is benzyl.
[8]. A compound according to [1] above wherein $R^1$ is $(C_3$-$C_4)$alkyl.
[9]. A compound according to [1] above wherein $R^1$ is methyl.
[10]. A compound according to [1] above wherein $R^1$ is —$CH_2R^{10}$ and $R^{10}$ is $(C_4$-$C_6)$carbocycle.
[11]. A compound according to [1] above wherein $R^1$ is —$C(=O)(C_1$-$C_{10})$hydrocarbyl.
[12]. A compound according to [1] above wherein $R^1$ is —$C(=O)O(C_1$-$C_{10})$hydrocarbyl.
[13]. A compound according to [1] above wherein $R^1$ is —$C(=O)O(C_1$-$C_3)$hydrocarbyl.
[14]. A compound according to [1] above wherein $R^1$ is —$SO_2(C_1$-$C_{10})$hydrocarbyl.
[15]. A compound according to [1] above wherein $R^1$ is —$SO_2(C_1$-$C_8)$hydrocarbyl.
[16]. A compound according to [1] above wherein $R^1$ is —$SO_2(C_1$-$C_3)$alkyl.
[17]. A compound according to any of [1] through [16] above wherein $R^2$ is hydrogen.
[18]. A compound according to any of [1] through [16] above wherein $R^2$ is halogen.
[19]. A compound according to any of [1] through [16] above wherein $R^2$ is $(C_1$-$C_4)$alkyl.
[20]. A compound according to any of [1] through [16] above wherein $R^2$ is fluoro$(C_1$-$C_4)$alkyl.
[21]. A compound according to any of [1] through [16] above wherein $R^2$ is nitro.
[22]. A compound according to any of [1] through [16] above wherein $R^2$ is —$SO_3H$.
[23]. A compound according to any of [1] through [16] above wherein $R^2$ is —$N^+HR^5R^6$.
[24]. A compound according to any of [1] through [16] above wherein $R^2$ is $(C_1$-$C_3)$alkyl.
[25]. A compound according to any of [1] through [16] above wherein $R^2$ is chloro.
[26]. A compound according to any of [1] through [16] above wherein $R^2$ is fluoro.
[27]. A compound according to any of [1] through [16] above wherein $R^2$ is trifluoromethyl.
[28]. A compound according to any of [1] through [16] above wherein $R^2$ is methyl.
[29]. A compound according to any of [1] through [16] above wherein $R^2$ is fluoro$(C_1$-$C_3)$alkyl.
[30]. A compound according to any of [1] through [29] above wherein $R^3$ is hydrogen.
[31]. A compound according to any of [1] through [29] above wherein $R^3$ is halogen.
[32]. A compound according to any of [1] through [29] above wherein $R^3$ is $(C_1$-$C_4)$alkyl.
[33]. A compound according to any of [1] through [29] above wherein $R^3$ is fluoro$(C_1$-$C_4)$alkyl.
[34]. A compound according to any of [1] through [29] above wherein $R^3$ is nitro.
[35]. A compound according to any of [1] through [29] above wherein $R^3$ is —$SO_3H$.
[36]. A compound according to any of [1] through [29] above wherein $R^3$ is —$N^+HR^5R^6$.
[37]. A compound according to any of [1] through [29] above wherein $R^3$ is $(C_1$-$C_3)$alkyl.
[38]. A compound according to any of [1] through [29] above wherein $R^3$ is chloro.
[39]. A compound according to any of [1] through [29] above wherein $R^3$ is fluoro.
[40]. A compound according to any of [1] through [29] above wherein $R^3$ is trifluoromethyl.
[41]. A compound according to any of [1] through [29] above wherein $R^3$ is methyl.
[42]. A compound according to any of [1] through [29] above wherein $R^3$ is fluoro$(C_1$-$C_3)$alkyl.
[43]. A compound according to any of [1] through [42] above wherein $R^4$ is hydrogen.
[44]. A compound according to any of [1] through [42] above wherein $R^4$ is halogen.
[45]. A compound according to any of [1] through [42] above wherein $R^4$ is $(C_1$-$C_4)$alkyl.
[46]. A compound according to any of [1] through [42] above wherein $R^4$ is fluoro$(C_1$-$C_4)$alkyl.
[47]. A compound according to any of [1] through [42] above wherein $R^4$ is nitro.
[48]. A compound according to any of [1] through [42] above wherein $R^4$ is —$SO_3H$.
[49]. A compound according to any of [1] through [42] above wherein $R^4$ is —$N^+HR^5R^6$.

[50]. A compound according to any of [1] through [42] above wherein $R^4$ is $(C_1-C_3)$alkyl.
[51]. A compound according to any of [1] through [42] above wherein $R^4$ is chloro.
[52]. A compound according to any of [1] through [42] above wherein $R^4$ is fluoro.
[53]. A compound according to any of [1] through [42] above wherein $R^4$ is trifluoromethyl.
[54]. A compound according to any of [1] through [42] above wherein $R^4$ is methyl.
[55]. A compound according to any of [1] through [42] above wherein $R^4$ is fluoro$(C_1-C_3)$alkyl.
[56]. A compound according to any of [1] through [55] above wherein $R^5$ is $(C_1-C_{10})$hydrocarbyl.
[57]. A compound according to any of [1] through [55] above wherein $R^5$ is fluoro$(C_1-C_{10})$hydrocarbyl.
[58]. A compound according to any of [1] through [55] above wherein $R^5$ is $(C_1-C_6)$hydrocarbyl.
[59]. A compound according to any of [1] through [55] above wherein $R^5$ is methyl.
[60]. A compound according to any of [1] through [59] above wherein $R^6$ is $(C_1-C_{10})$hydrocarbyl.
[61]. A compound according to any of [1] through [59] above wherein $R^5$ is fluoro$(C_1-C_{10})$hydrocarbyl.
[62]. A compound according to any of [1] through [59] above wherein $R^5$ is $(C_1-C_6)$hydrocarbyl.
[63]. A compound according to any of [1] through [59] above wherein $R^5$ is methyl.
[64]. A compound according to any of [1] through [59] above wherein $R^5$ is cyclopropylmethyl.
[65]. A compound according to any of [1] through [55] above wherein $R^5$ and $R^6$, taken together with the nitrogen to which they are attached, form a five-membered non-aromatic heterocycle.
[66]. A compound according to any of [1] through [55] above wherein $R^5$ and $R^6$, taken together with the nitrogen to which they are attached, form a six-membered non-aromatic heterocycle.
[67]. A compound according to any of [1] through [55] above wherein $R^5$ and $R^6$, taken together with the nitrogen to which they are attached, form a seven-membered non-aromatic heterocycle.
[68]. A compound according to any of [1] through [55] above wherein $R^5$ and $R^6$, taken together with the nitrogen to which they are attached, form a five-membered non-aromatic heterocycle, which is substituted with fluoro.
[69]. A compound according to any of [1] through [55] above wherein $R^5$ and $R^6$, taken together with the nitrogen to which they are attached, form a six-membered non-aromatic heterocycle, which is substituted with fluoro.
[70]. A compound according to any of [1] through [55] above wherein $R^5$ and $R^6$, taken together with the nitrogen to which they are attached, form a seven-membered non-aromatic heterocycle, which is substituted with fluoro.
[71]. A compound according to any of [1] through [55] above wherein $R^5$ and $R^6$, taken together with the nitrogen to which they are attached, form a five-membered non-aromatic heterocycle, which is substituted with $(C_1-C_4)$alkyl.
[72]. A compound according to any of [1] through [55] above wherein $R^5$ and $R^6$, taken together with the nitrogen to which they are attached, form a six-membered non-aromatic heterocycle, which is substituted with $(C_1-C_4)$alkyl.
[73]. A compound according to any of [1] through [55] above wherein $R^5$ and $R^6$, taken together with the nitrogen to which they are attached, form a seven-membered non-aromatic heterocycle, which is substituted with $(C_1-C_4)$alkyl.
[74]. A compound according to any of [1] through [55] above wherein $R^5$ and $R^6$, taken together with the nitrogen to which they are attached, form a five-membered non-aromatic heterocycle, which is substituted with fluoro and $(C_1-C_4)$alkyl.
[75]. A compound according to any of [1] through [55] above wherein $R^5$ and $R^6$, taken together with the nitrogen to which they are attached, form a six-membered non-aromatic heterocycle, which is substituted with fluoro and $(C_1-C_4)$alkyl.
[76]. A compound according to any of [1] through [55] above wherein $R^5$ and $R^6$, taken together with the nitrogen to which they are attached, form a seven-membered non-aromatic heterocycle, which is substituted with fluoro and $(C_1-C_4)$alkyl.
[77]. A compound according to any of [1] through [55], [65], [68], [71], and [74] above wherein $R^5$ and $R^6$, taken together with the nitrogen to which they are attached, form a pyrrolidine ring.
[78]. A compound according to any of [1] through [55], [65], and [77] above wherein $-NR^5R^6$ is

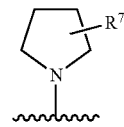

and $R^7$ is hydrogen.
[79]. A compound according to any of [1] through [55], [65], [68], and [77] above wherein $-NR^5R^6$ is

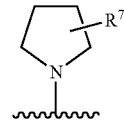

and $R^7$ is fluorine.
[80]. A compound according to any of [1] through [55], [65], [71], and [77] above wherein —NR5R6 is

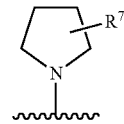

and $R^7$ is $(C_1-C_3)$alkyl.
[81]. A compound according to any of [1] through [80] above wherein $R^8$ is hydrogen.
[82]. A compound according to any of [1] through [80] above wherein $R^8$ is halogen.
[83]. A compound according to any of [1] through [80] above wherein $R^8$ is $(C_1-C_4)$alkyl.
[84]. A compound according to any of [1] through [80] above wherein $R^8$ is fluoro$(C_1-C_4)$alkyl.
[85]. A compound according to any of [1] through [80] above wherein $R^8$ is nitro.

[86]. A compound according to any of [1] through [80] above wherein $R^8$ is —SO$_3$H.

[87]. A compound according to any of [1] through [80] above wherein $R^8$ is —N$^+$HR$^5$R$^6$.

Throughout this specification the terms and substituents retain their definitions.

C$_1$ to C$_{10}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus (C$_3$-C$_{10}$) carbocycle refers to both non-aromatic and aromatic systems, including such systems as cyclopropane, benzene and cyclohexene; (C$_8$-C$_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, benzoxazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Loweracyl refers to groups containing one to four carbons.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino[HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine.

Substituents R" are generally defined when introduced and retain that definition throughout the specification and in all independent claims.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

The compounds described herein contain three asymmetric centers and may thus give rise to enantiomers, diastereomers, and other stereoisomeric forms which may be defined in terms of absolute stereochemistry as (R)- or (S)-. The present invention is meant to include all such possible isomers as racemates, optically pure forms and intermediate mixtures. Optically active isomers may be prepared using homo-chiral synthons or homo-chiral reagents, or optically resolved using conventional techniques such as chiral chromatography. All tautomeric forms are intended to be included. The graphic representations of racemic, ambiscalemic and scalemic or enantiomerically pure compounds used herein are taken from Maehr *J. Chem. Ed.* 62, 114-120 (1985): simple, single bond lines convey connectivity only and no stereochemical implication; solid and broken wedges are used to denote the absolute configuration of a chiral element; wavy lines indicate explicit disavowal of any stereochemical implication which the bond it represents could generate; solid and broken bold lines are geometric descriptors indicating the relative configuration shown but do not denote absolute configurations; and wedge outlines and dotted or broken lines denote enantiomerically pure compounds of indeterminate absolute configuration. Enantiomerically pure means greater than 80 ee, and preferably greater than 90 ee.

For example, the generic structure depicting the compounds of the invention:

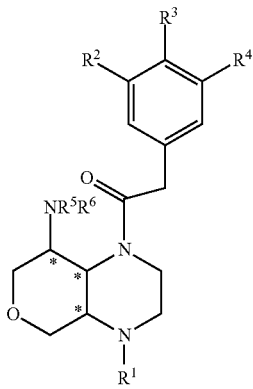

contains three asymmetric centers (labeled with asterisks). In one embodiment, the relative stereochemistry of the diastereomer can be represented as:

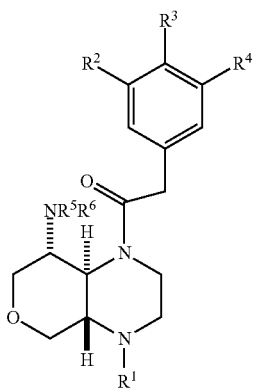

This representation indicates that the material is a mixture of isomers [(4aS,8R,8aR)-8-cyclopentyl-octahydro-1H-pyrano[3,4-b]pyrazine and (4aR,8S,8aS)-8-cyclopentyl-octahydro-1H-pyrano[3,4-b]pyrazine] in which the ring junction of the octahydro-1H-pyrano[3,4-b]pyrazine is trans and —NR⁵R⁶ is cis to its adjacent hydrogen at the ring junction. The mixture ratio of enantiomers can vary from approximately 1:1 (racemic) to approximately 90:10 (80% e.e.).

The representation:

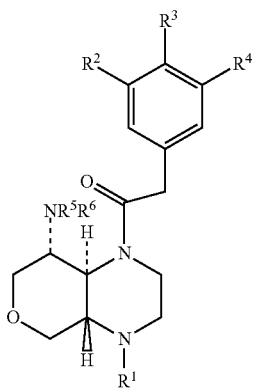

indicates a single enantiomer of the shown relative stereochemistry but unknown absolute stereochemistry, i.e. it could be either diastereomeric mirror image, as a substantially pure single enantiomer (e.g., approximately 80% e.e. to 99.99% e.e.).

The absolute stereochemistry of an enantiomer is represented as:

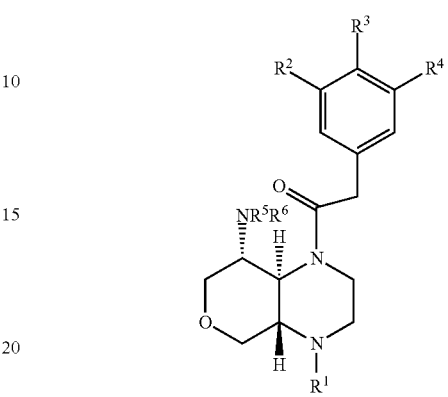

This graphical representation indicates that the shown enantiomer predominates over its mirror image, wherein the enantiomeric excess (e.e.) of the shown enantiomer is approximately 80% or higher (e.g., 80% to 99.99%).

As used herein, the terms "treatment" or "treating," or "palliating" or "ameliorating" refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic—as they are in most cases—salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic functionality (e.g. —SO₃H), suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

In general, compounds of formula I can be prepared as described below.

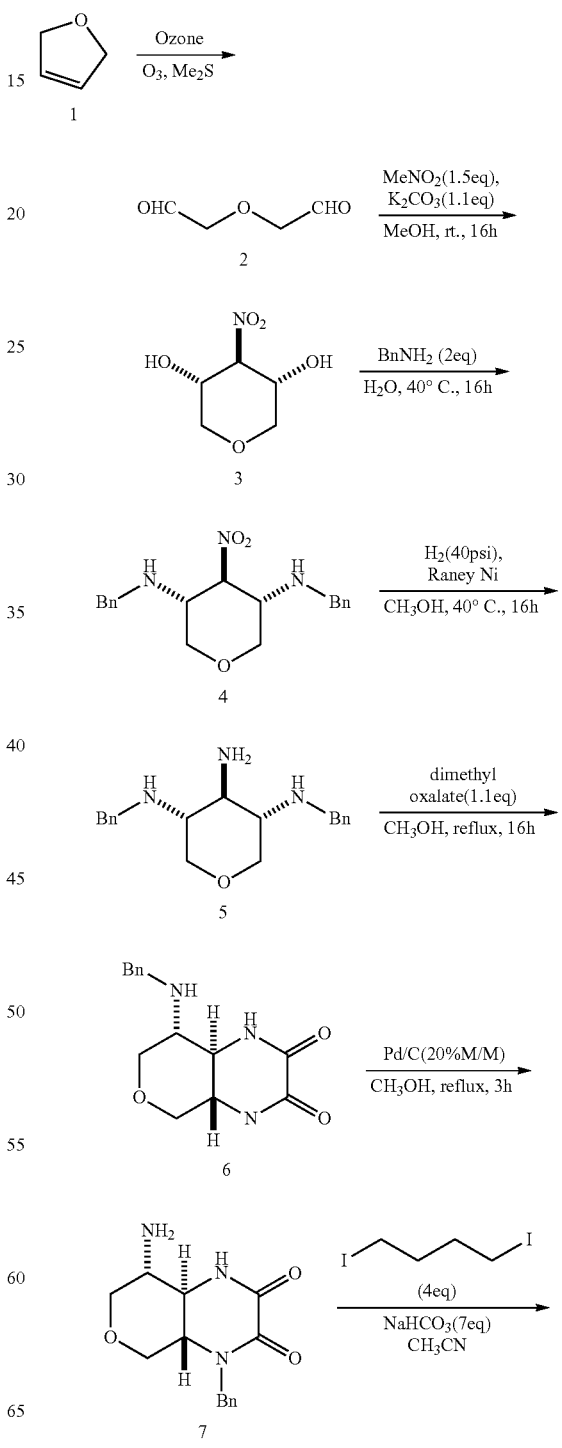

-continued
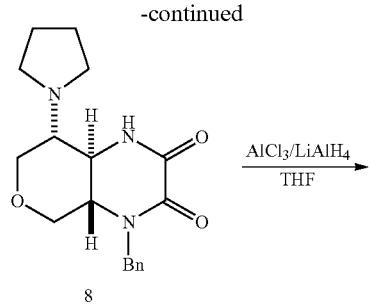
8
→ AlCl₃/LiAlH₄ / THF →
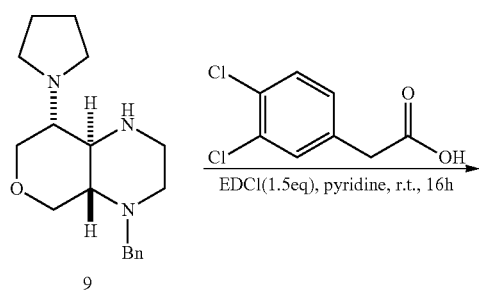
9
→ 3,4-dichlorophenylacetic acid, EDCl(1.5eq), pyridine, r.t., 16h →
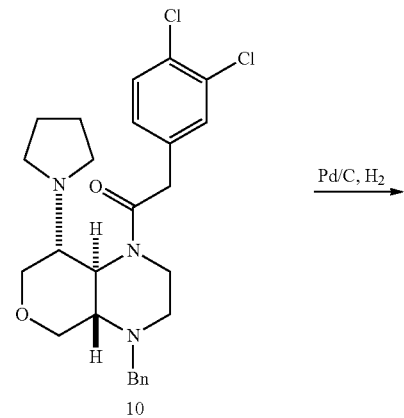
10
→ Pd/C, H₂ →
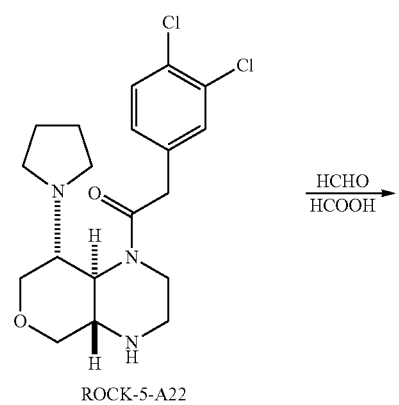
ROCK-5-A22
→ HCHO / HCOOH →
-continued
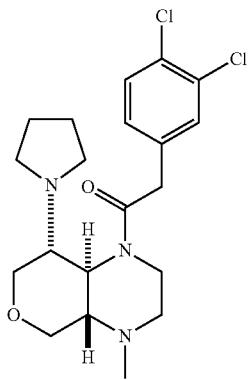
ROCK-5-A23
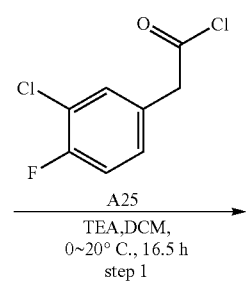
9
→ A25, TEA, DCM, 0~20° C., 16.5 h, step 1 →
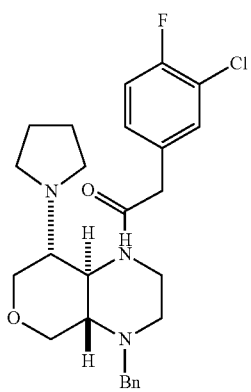
3_A25
→ Pd/C, H₂, THF/H₂O/HCl 1:1:0.2, step 2 →
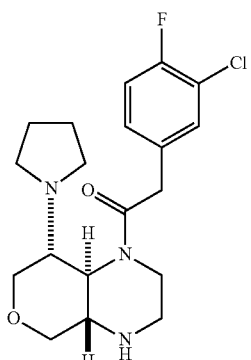
ROCK-5-A25

17
-continued

18
-continued

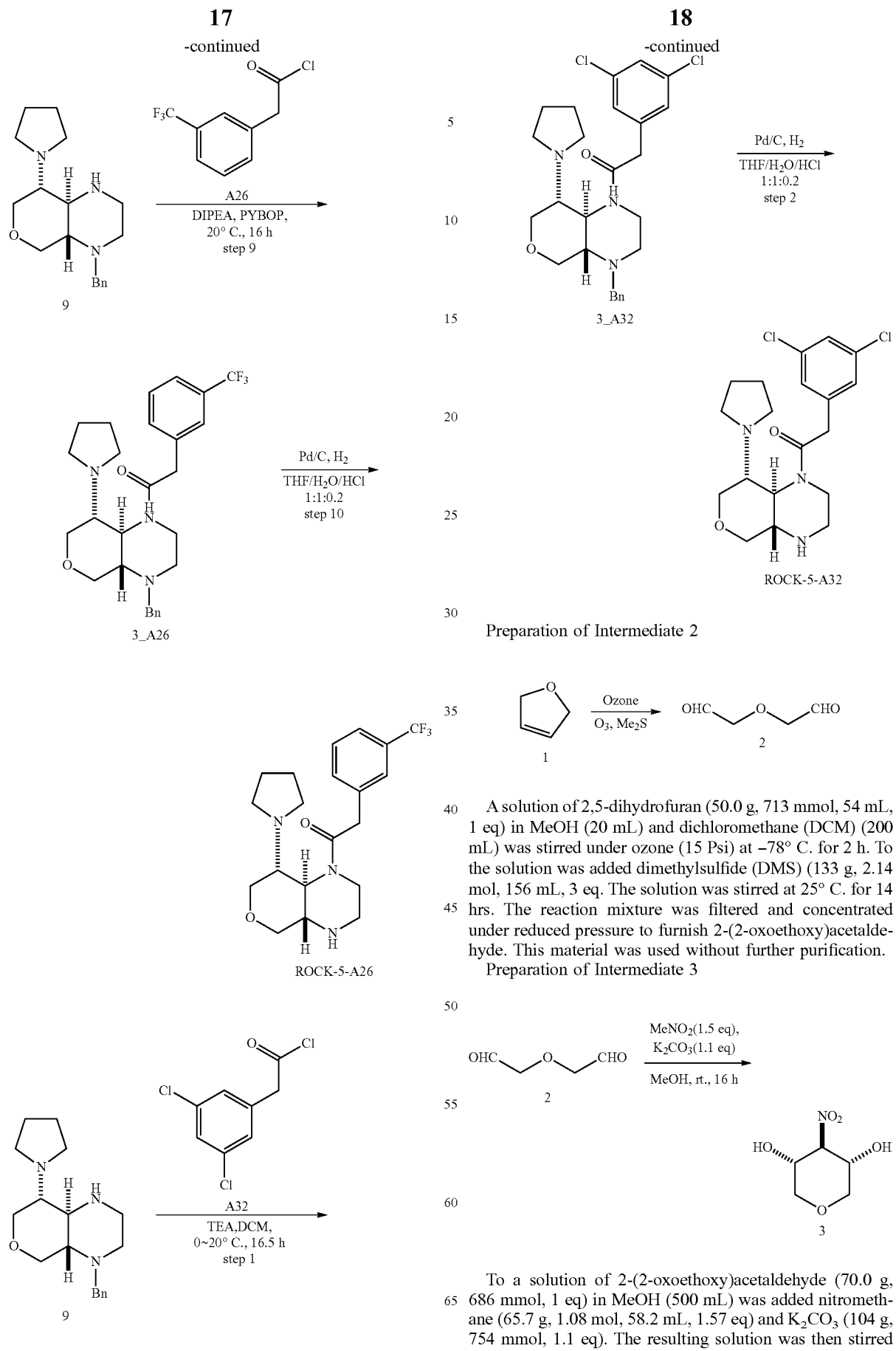

Preparation of Intermediate 2

A solution of 2,5-dihydrofuran (50.0 g, 713 mmol, 54 mL, 1 eq) in MeOH (20 mL) and dichloromethane (DCM) (200 mL) was stirred under ozone (15 Psi) at −78° C. for 2 h. To the solution was added dimethylsulfide (DMS) (133 g, 2.14 mol, 156 mL, 3 eq. The solution was stirred at 25° C. for 14 hrs. The reaction mixture was filtered and concentrated under reduced pressure to furnish 2-(2-oxoethoxy)acetaldehyde. This material was used without further purification.

Preparation of Intermediate 3

To a solution of 2-(2-oxoethoxy)acetaldehyde (70.0 g, 686 mmol, 1 eq) in MeOH (500 mL) was added nitromethane (65.7 g, 1.08 mol, 58.2 mL, 1.57 eq) and $K_2CO_3$ (104 g, 754 mmol, 1.1 eq). The resulting solution was then stirred for 3 hr at 0° C. The solution was warmed to 25° C., and then stirred at 25° C. for 13 hrs. TLC(DCM:MeOH=10:1, Rf=0.6) indicated intermediate 2 was completely consumed. The reaction mixture was filtered and concentrated under reduced pressure which provided 4-nitrotetrahydropyran-3,5-diol as a yellow solid.

Preparation of Intermediate 4

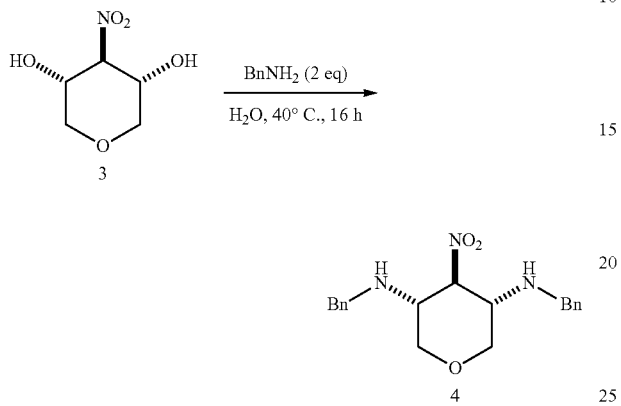

To a solution of 4-nitrotetrahydropyran-3,5-diol (15.0 g, 92 mmol, 1 eq) in H$_2$O (110 mL) was added benzylamine (BnNH$_2$) (19.7 g, 183.9 mmol, 20.1 mL, 2 eq). The resulting solution was stirred at 40° C. for 16 hr. The reaction mixture was filtered and concentrated under reduced pressure to give a residue. The residue was purified by preparative HPLC which provided N3,N5-dibenzyl-4-nitro-tetrahydropyran-3,5-diamine as a yellow oil. LC/MS m/z 342.2 (M+H).

Preparation of Intermediate 5

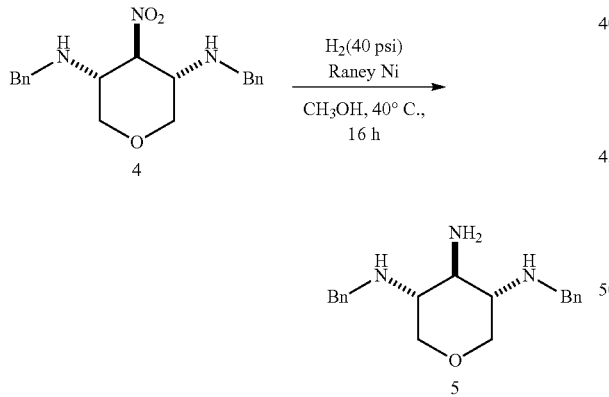

To a solution of N3,N5-dibenzyl-4-nitro-tetrahydropyran-3,5-diamine (5.00 g, 14.7 mmol, 1 eq) in MeOH (10 mL) was added Raney-Ni (1.25 g, 14.7 mmol, 1 eq). The solution was stirred under H$_2$ (45 Psi) at 25° C. for 16 hr. The reaction mixture was filtered and concentrated under reduced pressure which provided N3,N5-dibenzyltetrahydropyran-3,4,5-triamine as a yellow oil. $^1$H-NMR (400 MHz, DMSO-d$_6$): δ 7.36-7.19 (10H, m), 3.91-3.78 (2H, m), 3.78-3.70 (2H, m), 3.65 (2H, d, J=13.7 Hz), 2.88 (2H, t, J=10.5 Hz), 2.29-1.90 (6H, m). LC/MS m/z 312.3 (M+H).

Preparation of Intermediate 6

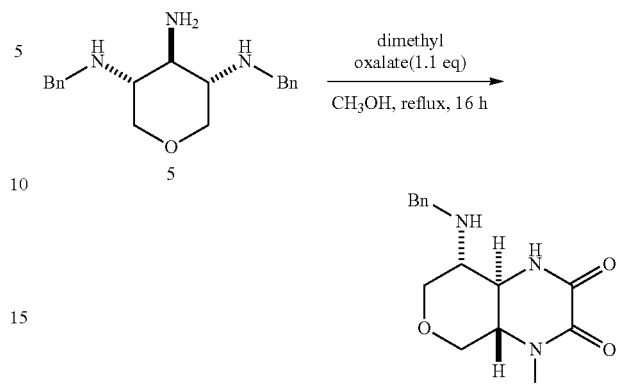

To a solution of N3,N5-dibenzyltetrahydropyran-3,4,5-triamine (3.10 g, 9.95 mmol, 1 eq) in MeOH (30 mL) was added dimethyl oxalate (1.17 g, 9.95 mmol, 1 eq). The resulting solution was stirred at 66° C. for 16 hr. The reaction mixture was filtered and dried in vacuo which provided 4-benzyl-8-(benzylamino)-1,4a,5,7,8,8a-hexahydropyrano[3,4-b]pyrazine-2,3-dione as a white solid. LC/MS m/z=366.3 (M+H).

Preparation of Intermediate 7

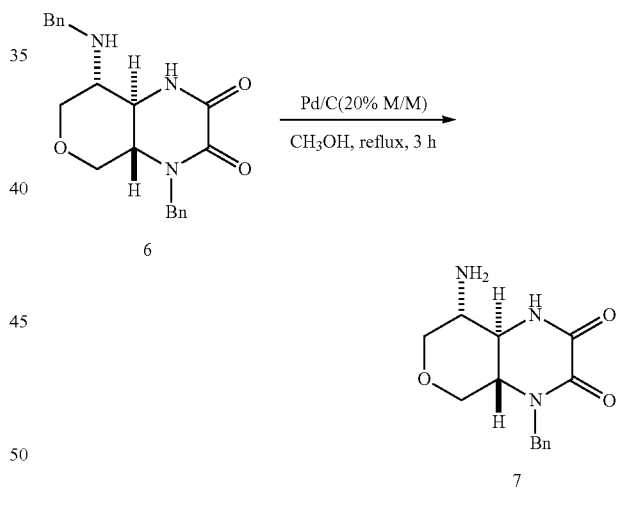

To a solution of 4-benzyl-8-(benzylamino)-1,4a,5,7,8,8a-hexahydropyrano[3,4-b]pyrazine-2,3-dione (2.70 g, 7.39 mmol, 1 eq) in MeOH (50 mL) was added Pd/C (1.35 g) and ammonium formate (4.66 g, 73.9 mmol, 10 eq). The solution was stirred at 65° C. for 3 hr. The reaction mixture was filtered and concentrated under reduced pressure which provided 8-amino-4-benzyl-1,4a,5,7,8,8a-hexahydropyrano[3,4-b]pyrazine-2,3-dione as a white solid. $^1$H-NMR (400 MHz, methanol-d$_4$): δ 7.39-7.33 (2H, m), 7.32-7.24 (3H, m), 4.95-4.89 (2H, m), 4.55 (1H, d, J=15.9 Hz), 4.13 (1H, dd, J=4.3, 10.9 Hz), 3.87 (1H, dd, J=5.0, 11.2 Hz), 3.69 (1H, dt, J=4.3, 10.7 Hz), 3.43 (1H, t, J=10.4 Hz), 3.29-3.21 (1H, m), 3.05 (1H, t, J=11.0 Hz), 2.84-2.75 (1H, m). LC/MS m/z 276.3 (M+H).

Preparation of Intermediate 8

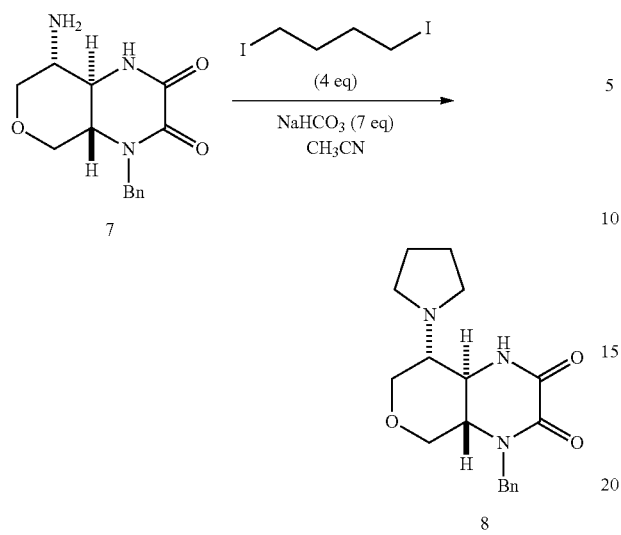

To a solution of 8-amino-4-benzyl-1,4a,5,7,8,8a-hexahydropyrano[3,4-b]pyrazine-2,3-dione (2.00 g, 7.26 mmol, 1 eq) in CH$_3$CN (50 mL) was added NaHCO$_3$ (4.15 g, 49.4 mmol, 1.92 mL, 6.8 eq) and 1,4-diiodobutane (9.00 g, 29.0 mmol, 3.81 mL, 4 eq). The solution was stirred at 82° C. for 18 hr. The reaction mixture was filtered and concentrated under reduced pressure which provided 4-benzyl-8-pyrrolidin-1-yl-1,4a,5,7,8,8a-hexahydropyrano [3,4-b]pyrazine-2,3-dione as a white solid. $^1$H-NMR (400 MHz, methanol-d$_4$): δ 7.39-7.33 (2H, m), 7.32-7.24 (3H, m), 4.93 (1H, d, J=15.8 Hz), 4.51 (1H, d, J=15.8 Hz), 4.14-4.00 (2H, m), 3.79-3.67 (2H, m), 3.45 (1H, t, J=11.0 Hz), 3.28-3.23 (1H, m), 2.97 (1H, dt, J=4.4, 10.5 Hz), 2.84-2.76 (2H, m), 2.75-2.67 (2H, m), 1.83-1.71 (4H, m). LC/MS m/z 330.0 (M+H).

Preparation of Intermediate 9

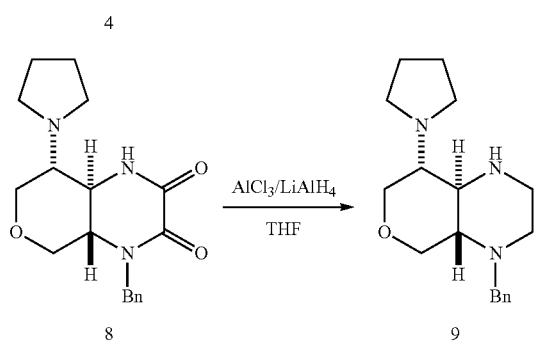 [SMILES: O=C1N[C@H]2[C@@H](COC[C@@H]2N2CCCC2)N(Cc2ccccc2)C1=O ; c1ccc(CN2CCN[C@H]3[C@H]2COC[C@@H]3N2CCCC2)cc1 ; "THF"]

To a solution of AlCl$_3$ (1.19 g, 8.89 mmol, 486 μL, 1.83 eq) in THF (30 mL) was added LiAlH$_4$ (1.03 g, 27.0 mmol, 5.56 eq) at 0° C. The solution was stirred at 25° C. for 30 min. To this solution was added 4-benzyl-8-pyrrolidin-1-yl-1,4a,5,7,8,8a-hexahydropyrano[3,4-b]pyrazine-2,3-dione (1.60 g, 4.86 mmol, 1 eq) at 0° C. The solution was stirred at 0° C. for 1 hr and then at 25° C. for 30 min. To the solution was added NaOH (2 M) until pH=8. The solution was extracted with ethyl acetate (3×30 mL). The organic layer was then dried (Na$_2$SO$_4$), filtered, and concentrated in vacuo which provided 4-Benzyl-8-pyrrolidin-1-yl-1,2,3,4a,5,7,8,8a-octahydropyrano[3,4-b]pyrazine as a yellow oil. LC/MS m/z 302.3 (M+H).

Preparation of ROCK-5-A53

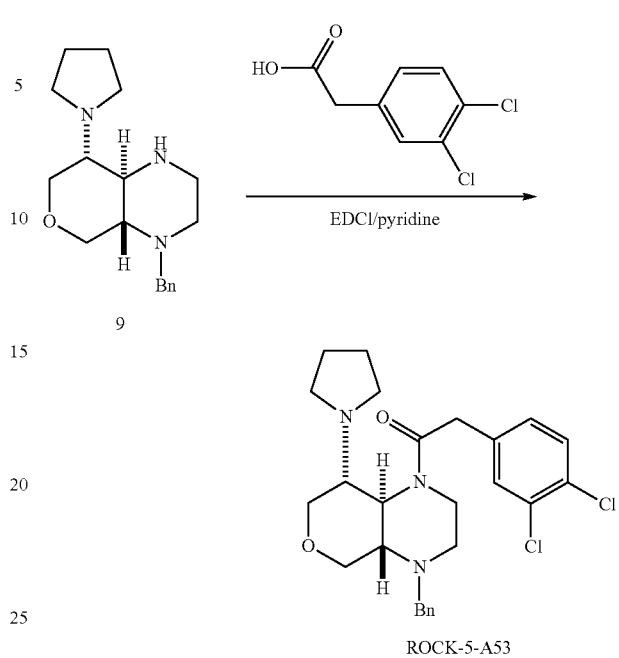

To a solution of 2-(3,4-dichlorophenyl)acetic acid (591 mg, 2.88 mmol, 1.1 eq) in pyridine (20 mL) was added 1-ethyl-3-(3-dimethylaminopropyl)carbodiimide (754 mg, 3.93 mmol, 1.5 eq). The resulting solution was stirred at 25° C. for 30 min. To this solution was added 4-benzyl-8-pyrrolidin-1-yl-1,2,3,4a,5,7,8,8a-octahydropyrano[3,4-b]pyrazine (790 mg, 2.62 mmol, 1 eq), and the resulting solution was stirred at 25° C. for 15.5 hr. The reaction mixture was quenched by addition of 5 mL of H$_2$O at 25° C. The mixture was diluted with 40 mL H$_2$O and extracted with 60 mL ethyl acetate (20 mL×3). The combined organic layers were dried over Na$_2$SO$_4$, filtered and concentrated under reduced pressure which provided 1-[4-benzyl-8-pyrrolidin-1-yl-3,4a,5,7,8,8a-hexahydro-2H-pyrano(3,4-b)pyrazin-1-yl]-2-(3,4-dichlorophenyl)ethanone as a yellow oil. LC/MS m/z 488.0 (M+H). $^1$H NMR (400 MHz, methanol-d$_4$, TFA salt) δ=7.50-7.28 (m, 7H), 7.21 (dd, J=2.0, 8.3 Hz, 1H), 4.95-4.87 (m, 1H), 4.84-4.76 (m, 1H), 4.50 (dd, J=5.0, 11.2 Hz, 1H), 4.34 (dd, J=4.4, 11.2 Hz, 1H), 4.12-4.02 (m, 2H), 3.92-3.76 (m, 3H), 3.67-3.44 (m, 6H), 3.40-3.33 (m, 2H), 3.16-3.01 (m, 1H), 2.85 (td, J=3.4, 12.1 Hz, 1H), 2.42-2.32 (m, 1H), 2.05 (br s, 4H)

Preparation of ROCK-5-A22

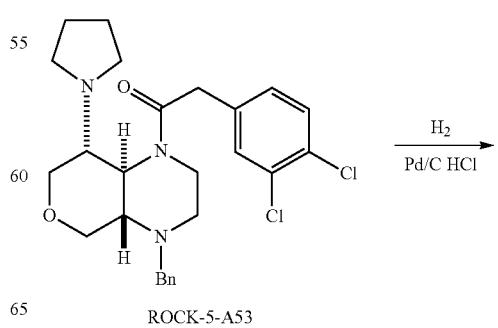

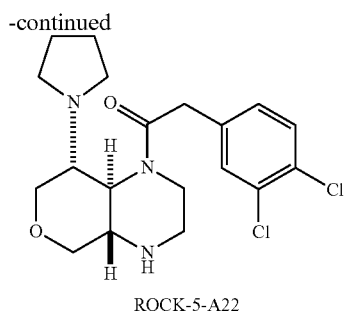

ROCK-5-A22

To a solution of palladium on carbon (Pd/C) (1.42 g, 10% wt % Pd) in THF (20 mL) and H₂O (20 mL) was added 1-[4-benzyl-8-pyrrolidin-1-yl-3,4a,5,7,8,8a-hexahydro-2H-pyrano(3,4-b)pyrazin-1-yl]-2-(3,4-dichlorophenyl)ethanone (710 mg, 1.45 mmol, 1 eq) and HCl (37%, 14.00 mL). The solution was stirred at 25° C. for 40 min under (1 bar) H₂. The reaction mixture was quenched by addition of 40 mL sat. aqueous NaHCO₃ at 25° C. The mixture was filtered. The solution was extracted with DCM 150 mL (50 mL×3). The combined organic layers were dried over Na₂SO₄, filtered, and concentrated under reduced pressure which provided 1-[8-pyrrolidin-1-yl-2,3,4,4a,5,7,8,8a-octahydro-pyrano(3,4-b) pyrazin-1-yl]-2-(3,4-dichlorophenyl)ethanone as a yellow solid. $^1$H-NMR (400 MHz, methanol-d₄): δ 7.48-7.44 (2H, m), 7.23 (1H, dd, J=2.1, 8.2 Hz), 4.07 (1H, dd, J=4.5, 11.2 Hz), 3.97 (1H, m, J=13.6 Hz), 3.91-3.80 (2H, m), 3.69 (1H, m, J=15.6 Hz), 3.35 (1H, s), 3.28-3.18 (2H, m), 3.18-3.09 (1H, m), 3.08-2.90 (4H, m), 2.70 (5H, m), 2.16 (1H, s), 1.72-1.67 (4H, m). LC/MS m/z 398.2 (M+H).

Preparation of ROCK-5-A23

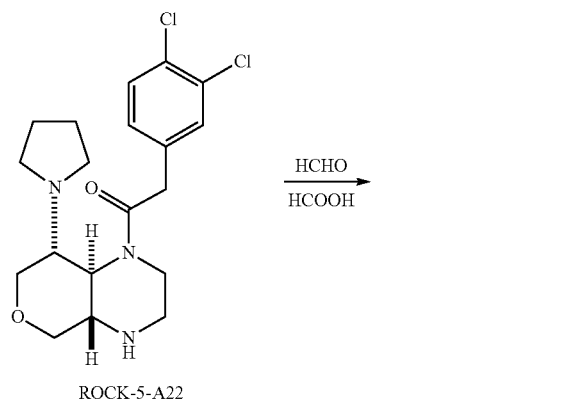

To a solution 1-[8-pyrrolidin-1-yl-2,3,4,4a,5,7,8,8a-octahydropyrano(3,4-b)pyrazin-1-yl]-2-(3,4-dichlorophenyl)ethanone (100 mg, 251 μmol, 1 eq) in HCOOH (2 mL) was added HCHO (326 mg, 4.02 mmol, 299 μL, 16 eq). The resulting solution was stirred at 80° C. for 2 hrs. The reaction mixture was concentrated under reduced pressure. The residue was diluted with NaHCO₃ (20 mL) and extracted with ethyl acetate 30 mL (10 mL×3). The combined organic layers were dried over Na₂SO₄, filtered, and concentrated under reduced pressure to furnish 1-[4-methyl-8-pyrrolidin-1-yl-3,4a,5,7,8,8a-hexahydro-2H- -pyrano(3,4-b)pyrazin-1-yl]-2-(3,4-dichlorophenyl)ethanone as a yellow oil. $^1$H-NMR (400 MHz, methanol-d₄) δ 8.49 (1H, s), 7.48 (2H, d, J=8.3 Hz), 7.23 (1H, dd, J=2.0, 8.3 Hz), 4.23 (2H, dt, J=4.9, 10.9 Hz), 4.10-4.02 (1H, m), 3.89-3.75 (2H, m), 3.43-3.37 (3H, m), 3.37-3.34 (3H, m), 3.21-3.15 (4H, m), 2.85 (1H, dt, J=2.7, 11.8 Hz), 2.45 (1H, dt, J=5.1, 10.0 Hz), 2.22 (3H, s), 1.95-1.87 (4H, m). LC/MS m/z 412.1 (M+H).

Preparation of Intermediate 3A25

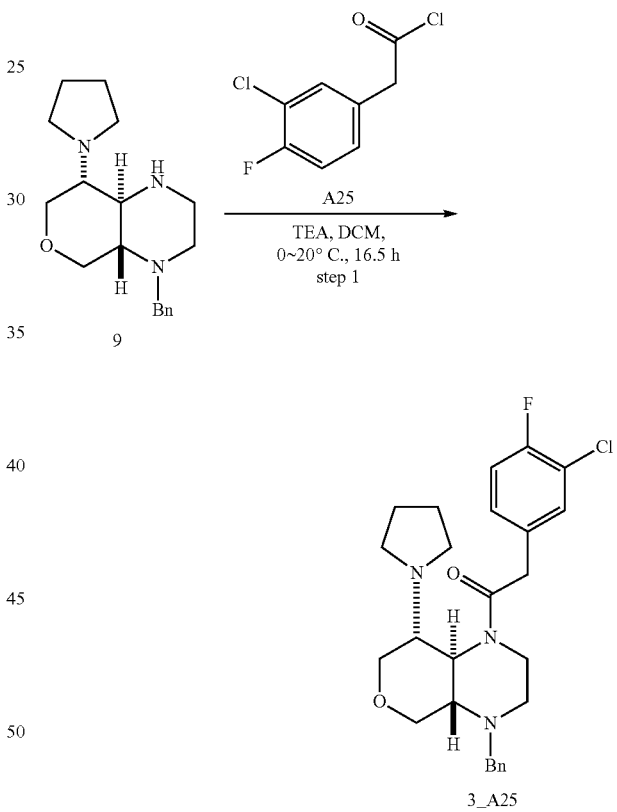

To a mixture of intermediate 9 (23 mg, 76 μmol, 1 eq) and triethylamine (TEA) (23 mg, 229 mol, 32 μL, 3 eq) in DCM (1.5 mL) was added a solution of A25 (47 mg, 229 μmol, 3 eq) in DCM (0.5 mL) dropwise at 0° C. under N₂. The mixture was stirred at 0° C. for 30 min and then warmed to 20° C. The mixture was stirred for 16 hours at 20° C. The mixture was concentrated under reduced pressure. The residue was purified by flash chromatography (column height: 250 mm, diameter: 100 mm, 100-200 mesh silica gel, dichloromethane:methanol=10/1) to obtain intermediate 3A25 as a yellow solid. LCMS: m/z=472.2 (M+H⁺).

Preparation of ROCK-5-A25

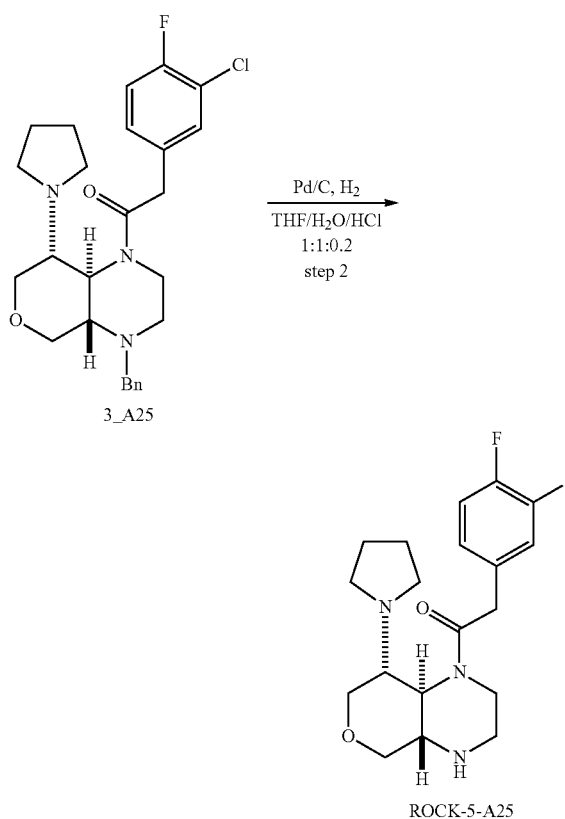

3_A25

ROCK-5-A25

To a solution of intermediate 3A25 (22 mg, 47 μmol, 1 eq) in THF (1.5 mL) and H$_2$O (1.5 mL) was added Pd/C (10 mg, 10 wt % Pd) and concentrated HCl (1.41 mL) under N$_2$. The suspension was degassed under vacuum and purged with H$_2$ several times. The mixture was stirred under H$_2$ (15 psi) at 20° C. for 20 mins. The reaction mixture was filtered. The filtrate was diluted with H$_2$O (50 mL) and neutralized with saturated NaHCO$_3$ (1 mL). The mixture was extracted with ethyl acetate (20 mL×3. The combined organic layers were washed with brine (10 mL), dried with anhydrous Na$_2$SO$_4$, and concentrated. The residue was purified by prep-HPLC (column: YMC-Actus Triart C18 100×30 mm×5 μm; mobile phase: [water (10 mM NH$_4$HCO$_3$)-ACN]; B %: 20%-40%, 12 min). ROCK-5-A25 was obtained as a light yellow solid. H-NMR: (400 MHz, chloroform-d) δ=7.32 (br d, J=6.36 Hz, 1H) 7.18-7.20 (m, 1H) 7.14 (br s, 1H) 7.04-7.11 (m, 1H) 7.04-7.04 (m, 1H) 7.01-7.01 (m, 1H) 4.29 (br s, 1H) 4.12 (br d, J=6.97 Hz, 1H) 3.57-3.94 (m, 5H) 3.18-3.39 (m, 2H) 2.88-3.17 (m, 5H) 2.75 (br s, 5H) 1.72 (br s, 5H). LCMS: m/z=382.0 (M+H$^+$)

Preparation of Intermediate 3A26

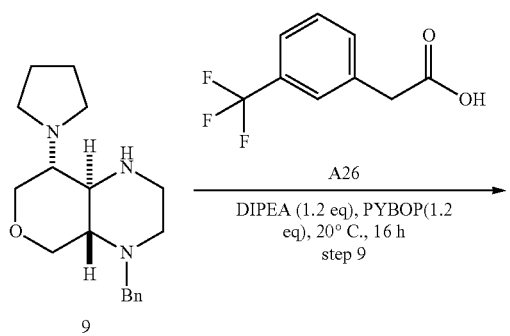

-continued

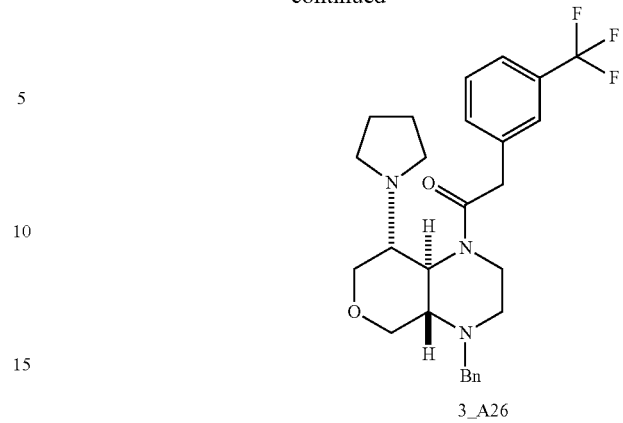

3_A26

To a mixture of A26 (28 mg, 139 μmol, 1.2 eq) and intermediate 9 (35 mg, 116 μmol, 1 eq) in DCM (2.5 mL) was added benzotriazol-1-yl-oxytripyrrolidinophosphonium hexafluorophosphate (PyBOP) (73 mg, 139 μmol, 1.2 eq) and N.N-diisopropylethylamine (DIPEA) (18 mg, 139 μmol, 24 μL, 1.2 eq) at 20° C. under N$_2$. The mixture was stirred at 20° C. for 16 hours. The mixture was concentrated under reduced pressure. The residue was purified by silica gel chromatography (column height: 250 mm, diameter: 100 mm, 100-200 mesh silica gel, petroleum ether:ethyl acetate=1:1) to obtain intermediate 3_A26 as a light yellow solid. H-NMR: (400 MHz, chloroform-d) δ=7.32-7.43 (m, 2H) 7.03-7.12 (m, 1H) 3.59-3.75 (m, 6H) 3.36-3.62 (m, 4H) 3.23-3.35 (m, 2H) 1.84 (br d, J=13.15 Hz, 3H) 1.45-1.72 (m, 1H) 1.45-1.72 (m, 4H) 1.30-1.43 (m, 1H) 1.30-1.44 (m, 1H) 1.29-1.44 (m, 1H) 1.25-1.26 (m, 1H) 0.78-0.95 (m, 2H). LCMS: m/z=488.2 (M+H$^+$).

Preparation of ROCK-5-A26

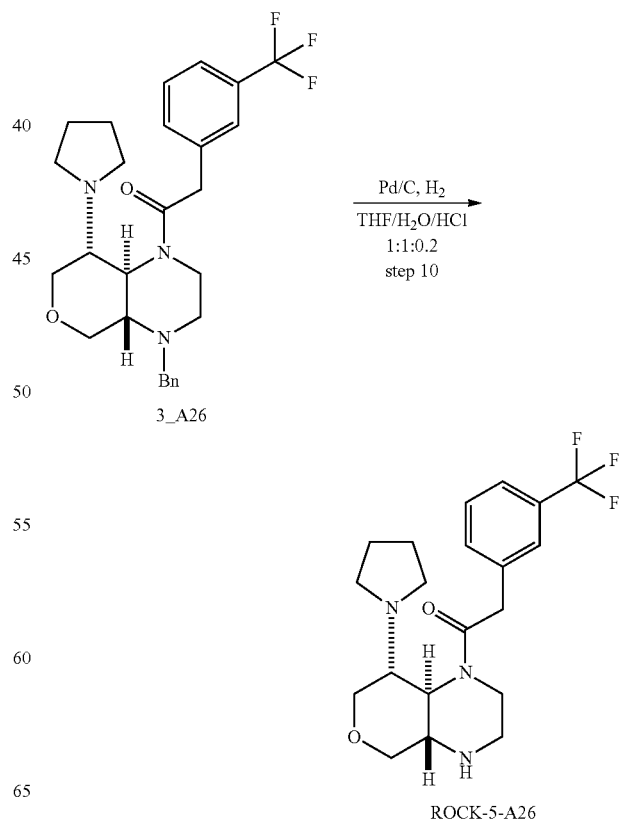

ROCK-5-A40 Scheme

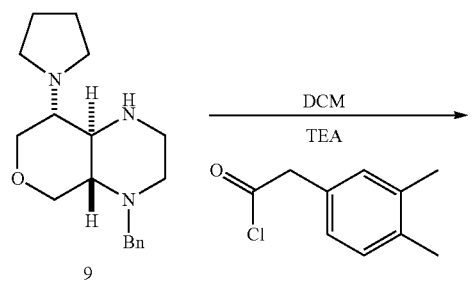

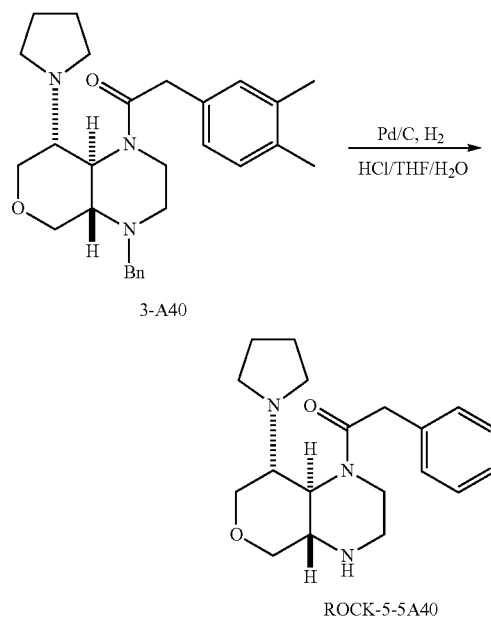

Preparation of 3-A40

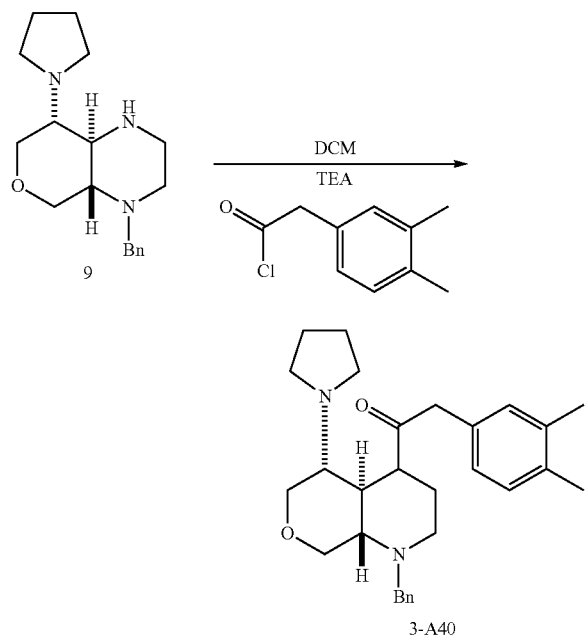

Intermediate 9 (50 mg, 166 μmol) and TEA (168 mg, 1.66 mmol, 231 μL) were dissolved in DCM (5 mL) followed by the addition of the acid chloride (90.89 mg, 497.64 μmol). The resulting mixture was stirred at 25° C. under $N_2$ for 12 hours. The reaction mixture was concentrated under reduced pressure to remove solvent. The residue was diluted with EtOAc (10 mL) and adjusted pH 5 with HCl (2 N, 0.5 mL) solution. The aqueous phase was washed with EtOAc (10 mL×2), and then the pH was adjusted to 8 using an aqueous $NaHCO_3$ solution. The aqueous phase was extracted with EtOAc (10 mL×3). The combined organic layers were washed with brine (10 mL), dried over with $Na_2SO_4$, filtered and concentrated under reduced pressure. The material was used as is in the next step.

Preparation of ROCK-5-5A40

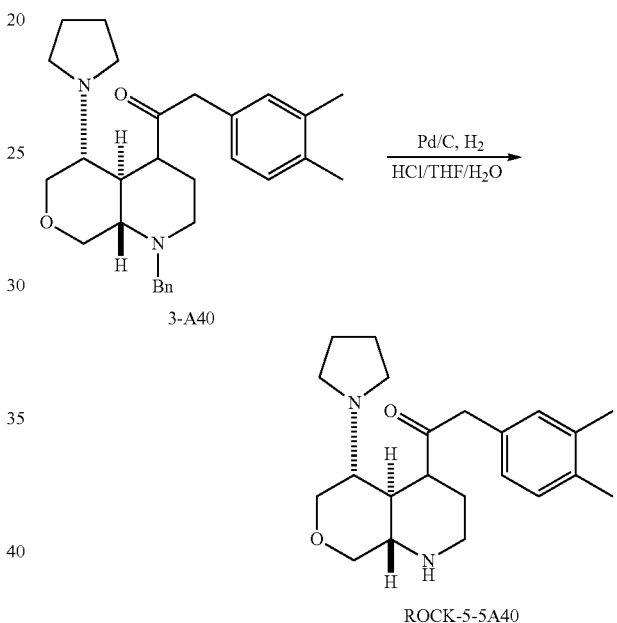

A solution of 3-A40 (50 mg, 112 μmol), Pd/C (20 mg, 10 wt % Pd), THF (10 mL), conc. HCl (0.3 mL), and $H_2O$ (10 mL) were stirred at 25° C. under $H_2$ (15 psi) for 12 hrs. The reaction mixture was filtered through a Celite pad, and the filtrate was concentrated under reduced pressure. The pH was adjusted to 8 with an aqueous NaHCO3 solution. The mixture was extracted with EtOAc (10 mL×3). The combined organic layers were washed with brine (10 mL), dried over with $Na_2SO_4$, filtered, and concentrated under reduced pressure. The residue was purified by prep-HPLC (TFA condition: column: Luna C18 100×30 5μ; mobile phase: [water (0.1% TFA)-ACN]; ACN %: 1%-35%, 10 min). Compound ROCK-5-A40 was obtained as a white solid. $^1$H NMR (400 MHz, methanol-$d_4$) δ=7.15-7.04 (m, 3H), 4.74 (dt, J=4.7, 10.3 Hz, 1H), 4.38 (dd, J=4.4, 11.7 Hz, 1H), 4.29-4.08 (m, 3H), 3.92-3.91 (m, 1H), 3.92-3.83 (m, 1H), 3.84-3.74 (m, 1H), 3.84-3.73 (m, 1H), 3.91-3.71 (m, 3H), 3.70-3.60 (m, 3H), 3.58-3.47 (m, 2H), 3.33 (br s, 1H), 2.84 (ddd, J=4.1, 9.4, 13.0 Hz, 1H), 2.25 (d, J=7.7 Hz, 6H), 2.02 (br s, 3H). LCMS (MH+): 358.2.

Preparation of ROCK-5-A44

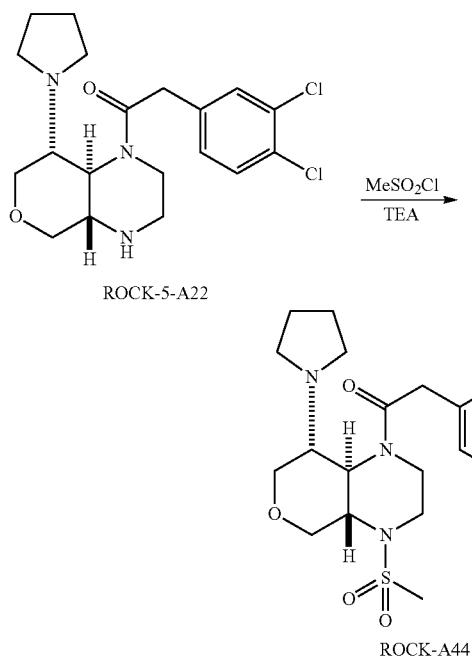

ROCK-5-A22

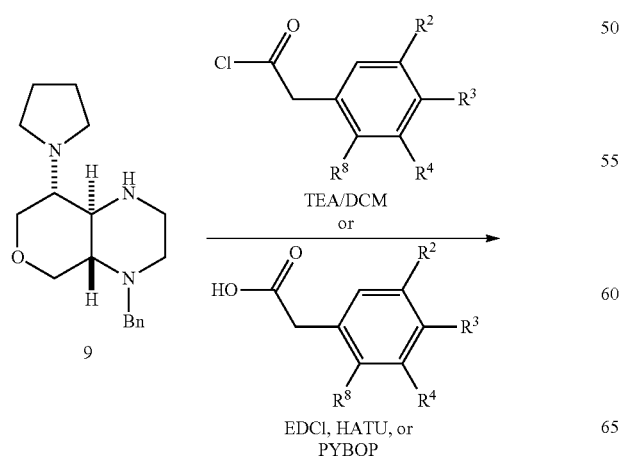

ROCK-A44

Rock-5-A22 (30 mg, 75 μmol) and methanesulfonyl chloride (17 mg, 151 umol, 12 μL) were taken up in DCM (3 mL). Triethylamine (38 mg, 377 μmol, 52 uL) was added to the reaction mixture. The reaction vessel was degassed and purged with $N_2$ (3 times). The mixture was stirred at 20° C. for 2 hours under a $N_2$ atmosphere. The reaction mixture was concentrated under reduced pressure to remove solvent. The residue was purified by prep-HPLC (TFA condition: Column: Nano-micro Kromasil C18 100*30 mm 5 μm; mobile phase: [water 0.1% TFA)-ACN]; %: ACN: 18%-38%, 10 min). ROCK-5-A44 was obtained as a white solid.

$^1$H NMR (400 MHz, methanol-$d_4$) δ7.51-7.44 (m, 2H), 7.22 (dd, J=1.9, 8.3 Hz, 1H), 4.37-4.29 (m, 2H), 4.28-4.16 (m, 2H), 3.94-3.87 (m, 4H), 3.83-3.72 (m, 3H), 3.70-3.55 (m, 3H), 3.47 (td, J=4.2, 12.7 Hz, 1H), 3.33 (br s, 1H), 2.94 (s, 3H), 2.11-1.89 (m, 4H). LCMS (MH+) 476.1.

Some compounds shown in Table A are made in similar fashion via the sequence shown in Scheme A:

Scheme A

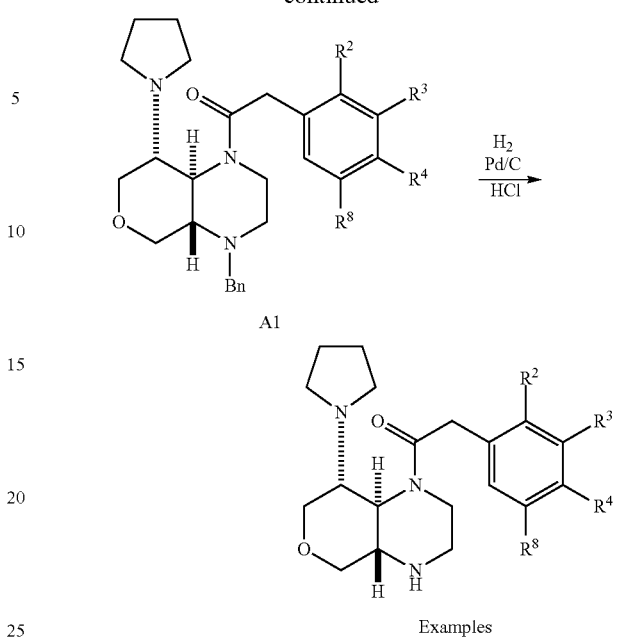

Some compounds shown in Table A are made via the sequence shown in Scheme B:

Scheme B

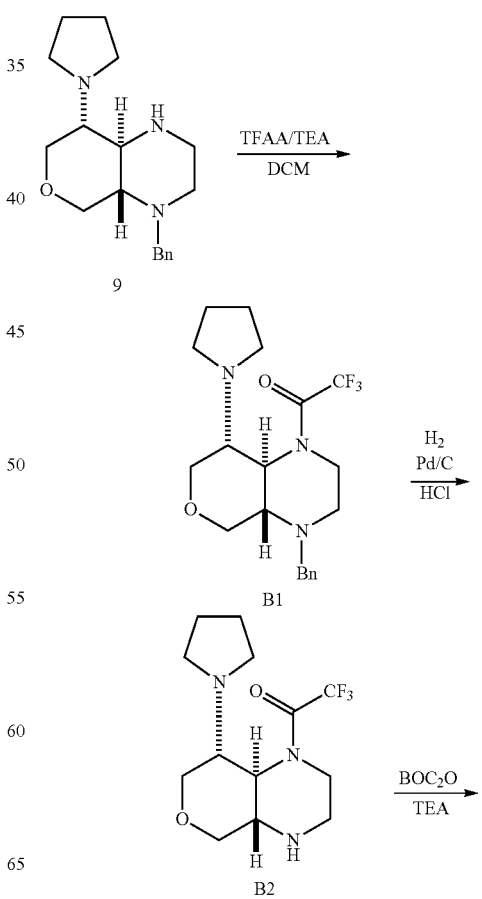

-continued

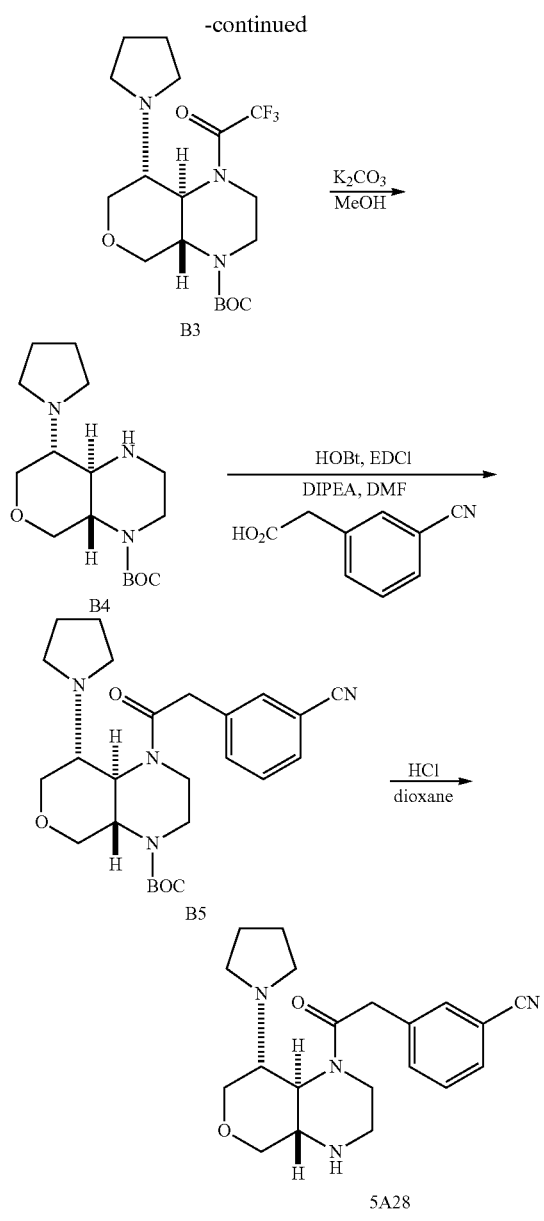

Example Experimentals for Scheme B:

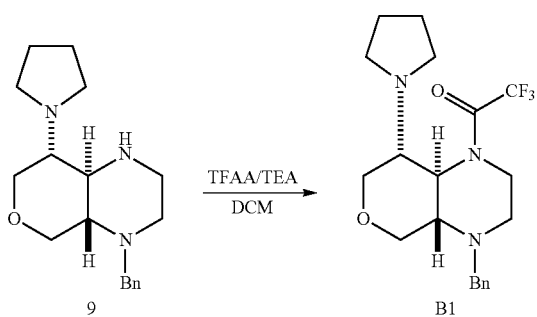

The amine 9 (1 g, 3.3 mmol, 1 eq) and TFAA (1.74 g, 8.3 mmol, 1.2 mL, 2.5 eq) were taken up in DCM (25 mL). Triethylamine (1.0 g, 10 mmol, 1.4 mL, 3 eq) and DMAP (41 mg, 330 μmol, 0.1 eq) were added to the reaction mixture. The mixture was degassed and purged with $N_2$ (3 times). The resulting mixture was stirred at 25° C. for 12 hours under a $N_2$ atmosphere. The reaction mixture was concentrated under reduced pressure. The residue was diluted with EtOAc (10 mL), and the pH was adjusted to 8 with aq. $NaHCO_3$. The aqueous phase was extracted with EtOAc (10 mL×2). The combined organic layers were washed with brine (10 mL) and dried over $Na_2SO_4$. The mixture was filtered and concentrated under reduced pressure. The residue was purified by column chromatography ($SiO_2$, Petroleum ether/Ethyl acetate=10/1 to 0:1) which furnished B1.

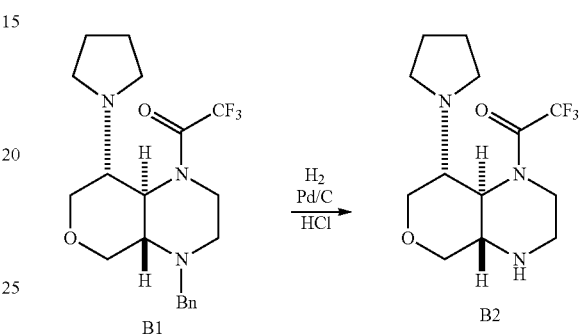

The amide B1 (950 mg, 2.39 mmol, 1 eq) and Pd/C (100 mg, 10 wt % Pd) were taken up in THF (15 mL), $H_2O$ (15 mL) and HCl (0.8 mL). The resulting solution was stirred at 25° C. under $H_2$ (15 psi) for 12 hrs. The reaction mixture was filtered and concentrated under reduced pressure. The residue was basified with aq. $NaHCO_3$ solution (pH=8). The aqueous solution was extracted with EtOAc 30 mL (10 mL×3). The combined organic layers were washed with brine (10 mL) and dried over $Na_2SO_4$. The mixture was filtered and concentrated under reduced pressure. The residue was purified by preparative-HPLC (basic condition: column: Agela Durashell C18 150×30 mm 5 μm; mobile phase: [water (0.04% $NH_3H_2O$)-ACN]; ACN gradient: 5%-35%, 10 min) which provided B2.

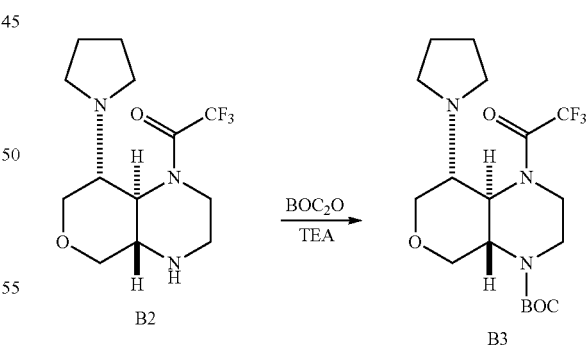

The amine B2 (700 mg, 2.28 mmol, 1 eq) and TEA (461 mg, 4.56 mmol, 634 μL, 2 eq) were taken up in DCM (20 mL) Di-tert-butyl dicarbonate (497 mg, 2.28 mmol, 523 μL, 1 eq) was added, and the resulting solution was stirred at 25° C. under $N_2$ for 12 hrs. The reaction mixture was concentrated under reduced pressure which provided the Boc protected amine B3. The material was used directly in the next step.

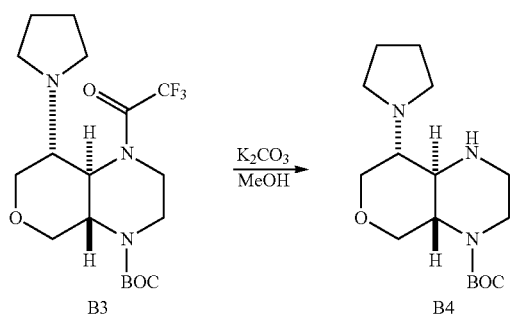

The Boc protected amine B3 (800 mg, 1.96 mmol, 1 eq) and K₂CO₃ (1.36 g, 9.82 mmol, 5 eq) were taken up in MeOH (20 mL) and H₂O (20 mL). The resulting mixture was stirred at 25° C. under N₂ for 12 hrs. The reaction mixture was concentrated under reduced pressure. The residue was purified by preparative TLC (SiO₂, DCM:MeOH=10:1 Rf=0.50) which provided amine B4.

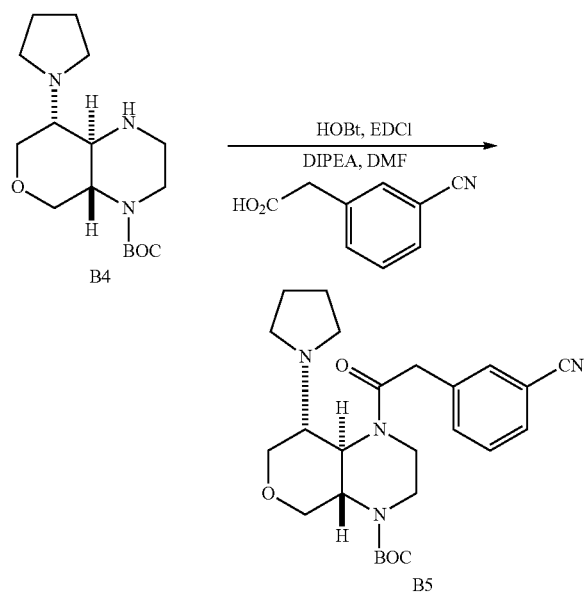

The amine B4 (19 mg, 116 μmol, 1.2 eq), HOBt (20 mg, 144 μmol, 1.5 eq), EDCI (28 mg, 144 μmol, 1.5 eq) and DIPEA (50 mg, 385 μmol, 67 μL, 4 eq) were dissolved in DMF (10 mL). 2-(3-Cyanophenyl)acetic acid (30 mg, 96 μmol, 1 eq) was added. The mixture was stirred at 25° C. under N₂ for 12 hrs. The reaction mixture was concentrated under reduced pressure to remove solvent. The residue was purified by preparative-HPLC (TFA condition: Column: UniSil 120×30 mm, 10 μm; mobile phase: [water (0.1% TFA)-ACN]; ACN %: 20%-50%, 11 min) which provided amide B5.

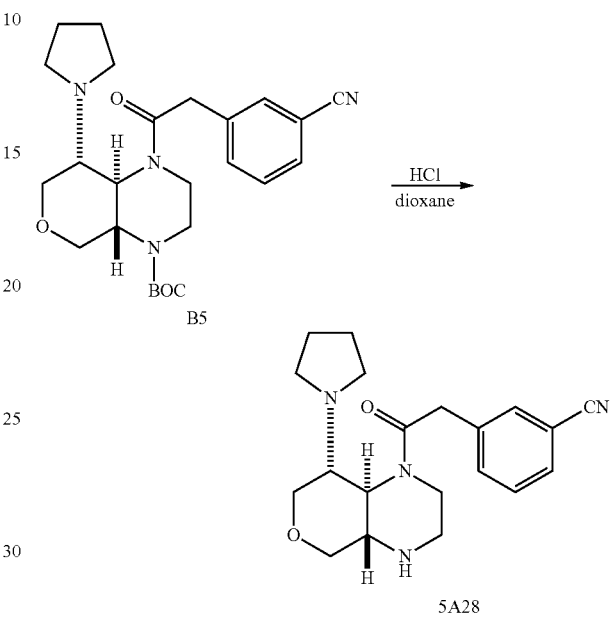

The amide B5 (17 mg, 37 μmol, 1 eq) was dissolved in dioxane (10 mL). Dioxane/HCl (10 mL, 4.0M) was added. The resulting mixture was stirred at 20° C. under N₂ for 6 hrs. The reaction mixture was concentrated under reduced pressure to remove solvent. The residue was purified by prep-HPLC (TFA condition: Column: Nano-micro Kromasil C18 100×30 mm, 5 μm; mobile phase: [water (0.1% TFA)-ACN]; ACN %: 5%-25%, 10 min) which provided 5A28 as the TFA salt. ¹H NMR (400 MHz, TFA salt, methanol-d₄) δ 7.72-7.61 (m, 3H), 7.56-7.51 (m, 1H), 4.70 (dt, J=4.4, 10.4 Hz, 1H), 4.39 (dd, J=4.5, 11.7 Hz, 1H), 4.32-4.21 (m, 2H), 4.15 (dd, J=5.2, 10.9 Hz, 1H), 3.98 (s, 2H), 3.90-3.64 (m, 4H), 3.60-3.50 (m, 3H), 3.38-3.34 (m, 2H), 2.03 (br s, 4H). LCMS (MH⁺) 355.1.

Table A shows spectroscopic data and synthons used to make various compounds via Schemes A and B.

TABLE A

| | | | Data | |
|---|---|---|---|---|
| Example | Structure | Reagent/Scheme | 1H NMR (400 MHz) | LCMS |
| 5A24 | (racemic) | Scheme A | (methanol-d₄) δ 7.35-7.22 (m, 4H), 4.08 (dd, J = 4.6, 11.2 Hz, 1H), 3.97 (br d, J = 13.2 Hz, 1H), 3.92-3.77 (m, 2H), 3.76-3.66 (m, 1H), 3.34 (s, 1H), 3.28-3.20 (m, 2H), 3.10-2.86 (m, 4H), 2.75 (br s, 4H), 2.70-2.59 (m, 1H), 1.77-1.67 (m, 4H) | (MH+) 364.1 |

TABLE A-continued

| Example | Structure | Reagent/Scheme | 1H NMR (400 MHz) | LCMS |
|---|---|---|---|---|
| 5A27 | (racemic) | Scheme A | (TFA salt, methanol-d$_4$) δ 7.41-7.35 (m, 1H), 7.18-7.12 (m, 2H), 7.06 (br t, J = 8.6 Hz, 1H), 4.72 (dt, J = 4.4, 10.3 Hz, 1H), 4.39 (dd, J = 4.5, 11.6 Hz, 1H), 4.26 (td, J = 4.3, 15.8 Hz, 1H), 4.20-4.09 (m, 2H), 3.94 (s, 2H), 3.84-3.76 (m, 1H), 3.71-3.61 (m, 3H), 3.56-3.49 (m, 2H), 3.40-3.35 (m, 2H), 3.17-3.02 (m, 1H), 2.04 (br s, 4H) | (MH+) 348.1 |
| 5A32 | (racemic) | Scheme A | (chloroform-d) δ = 7.19 (s, 2 H) 7.09 (d, J = 1.76 Hz, 1 H) 4.01-4.09 (m, 1 H) 3.74-3.82 (m, 1 H) 3.68-3.73 (m, 2 H) 3.63-3.68 (m, 2 H) 3.51-3.61 (m, 2 H) 3.13-3.36 (m, 3 H) 2.91-3.06 (m, 3 H) 2.89 (s, 1 H) 2.63-2.84 (m, 5 H) 1.72 (br s, 5H) | (MH+) 398.1 |
| 5A48 | (racemic) | Scheme B | (methanol-d$_4$) δ = 7.51 (dd, J = 2.1, 7.4 Hz, 1H), 7.35-7.27 (m, 2H), 4.70 (dt, J = 4.5, 10.2 Hz, 1H), 4.42-4.28 (m, 2H), 4.20-4.04 (m, 5H), 3.89-3.80 (m, 1H), 3.71-3.47 (m, 7H), 3.42-3.37 (m, 2H), 2.04 (br s, 4H) | (MH+) 398.1 |
| 5A46 | (racemic) | Scheme B | (TFA salt, methanol-d$_4$) δ = 7.73 (s, 1H), 7.61-7.48 (m, 2H), 4.71 (dt, J = 4.3, 10.3 Hz, 1H), 4.42-4.10 (m, 4H), 4.03-3.93 (m, 2H), 3.89-3.45 (m, 8H), 3.39 (ddd, J = 4.1, 9.3, 13.0 Hz, 2H), 2.01 (br s, 4H) | (MH+) 432.1 |
| 5A47 | (racemic) | Scheme A | (TFA salt, methanol-d$_4$) δ = 7.61 (s, 1H), 7.44 (br d, J = 7.7 Hz, 1H), 7.39-7.33 (m, 1H), 4.68 (dt, J = 4.6, 10.4 Hz, 1H), 4.37 (dd, J = 4.3, 11.6 Hz, 1H), 4.26 (br d, J = 16.0 Hz, 1H), 4.16-4.08 (m, 2H), 3.94 (s, 2H), 3.84-3.75 (m, 1H), 3.69-3.61 (m, 3H), 3.54-3.47 (m, 2H), 3.44 (br d, J = 12.7 Hz, 2H), 3.26-3.17 (m, 2H), 2.47 (s, 3H), 2.02 (br s, 4H) | (MH+) 412.2 |

TABLE A-continued

| Example | Structure | Reagent/Scheme | 1H NMR (400 MHz) | LCMS |
|---|---|---|---|---|
| 5A49 | (racemic) | Scheme A | (TFA salt, methanol-d₄) δ = 7.65 (br d, J = 7.9 Hz, 2H), 7.52 (br d, J = 8.1 Hz, 2H), 4.72 (br s, 1H), 4.44-4.07 (m, 4H), 4.00 (s, 2H), 3.83 (br s, 1H), 3.68 (br d, J = 10.3 Hz, 3H), 3.55 (br d, J = 10.5 Hz, 2H), 3.44 (br d, J = 10.6 Hz, 2H), 3.25-3.13 (m, 2H), 2.02 (br s, 4H) | (MH⁺) 398.1 |
| 5A57 | (racemic) | Scheme A | (TFA salt, 400 MHz, methanol-d₄) δ = 7.34-7.27 (m, 4H), 7.24 (br d, J = 7.6 Hz, 3H), 7.11 (d, J = 7.6 Hz, 1H), 4.78 (br s, 1H), 4.43 (br dd, J = 4.8, 11.4 Hz, 1H), 4.35-4.29 (m, 1H), 4.02 (br d, J = 13.8 Hz, 1H), 3.90 (br d, J = 13.4 Hz, 1H), 3.79 (br d, J = 10.0 Hz, 2H), 3.71 (br d, J = 17.6 Hz, 2H), 3.65-3.53 (m, 4H), 3.51-3.47 (m, 2H), 3.25 (br d, J = 13.4 Hz, 1H), 3.14 (t, J = 1.6 Hz, 1H), 2.82 (br s, 1H), 2.66 (br d, J = 12.3 Hz, 1H), 2.36 (s, 3H), 2.06 (br s, 4H) | (MH⁺) 378.3 |
| 5A58 | (racemic) | Scheme A | (TFA salt, methanol-d₄) δ = 7.37-7.31 (m, 1H), 7.29-7.24 (m, 1H), 7.18-7.11 (m, 1H), 4.71 (dt, J = 4.5, 10.3 Hz, 1H), 4.37 (dd, J = 4.5, 11.6 Hz, 1H), 4.30-4.08 (m, 3H), 3.90-3.77 (m, 3H), 3.73-3.62 (m, 3H), 3.58-3.49 (m, 2H), 3.44-3.35 (m, 3H), 3.17-3.04 (m, 1H), 2.40-2.33 (m, 3H), 2.02 (br s, 4H) | (MH⁺) 378.1 |
| 5A65 | (racemic) | Scheme A | (TFA salt, methanol-d₄) δ = 7.44 (t, J = 8.0 Hz, 1H), 7.25 (dd, J = 2.0, 10.3 Hz, 1H), 7.13 (d, J = 8.2 Hz, 1H), 4.70 (dt, J = 4.5, 10.3 Hz, 1H), 4.37 (dd, J = 4.5, 11.6 Hz, 1H), 4.29-4.08 (m, 3H), 3.91 (s, 2H), 3.84-3.75 (m, 1H), 3.70-3.61 (m, 3H), 3.57-3.48 (m, 2H), 3.47-3.39 (m, 2H), 3.20 (ddd, J = 4.2, 9.3, 13.0 Hz, 1H), 2.03 (br s, 4H) | (MH⁺) 382.2 |

TABLE A-continued

| Example | Structure | Reagent/Scheme | Data 1H NMR (400 MHz) | LCMS |
|---|---|---|---|---|
| 5A66 | 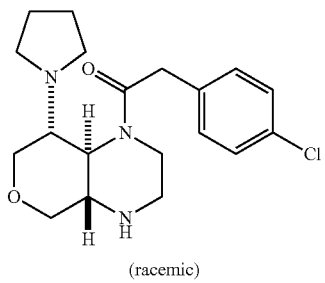 [SMILES: O=C(Cc1ccc(Cl)cc1)N1CCN[C@@H]2COC[C@H](N3CCCC3)[C@H]21] (racemic) | 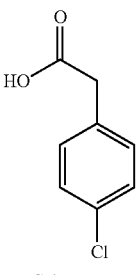 Scheme A | (TFA salt, methanol-d$_4$) δ = 7.39-7.28 (m, 4H), 4.72 (br s, 1H), 4.37 (br d, J = 7.7 Hz, 1H), 4.30-4.07 (m, 3H), 3.89 (br s, 2H), 3.79 (br d, J = 11.2 Hz, 1H), 3.66 (br t, J = 10.3 Hz, 3H), 3.59-3.49 (m, 2H), 3.38 (br d, J = 12.8 Hz, 3H), 3.08 (br s, 1H), 2.02 (br s, 4H) | (MH$^+$) 364.1 |

ROCK-5A52 is made via the sequence shown in Scheme C:

ROCK-5A55 and compounds shown in Table B are made as shown in Scheme D:

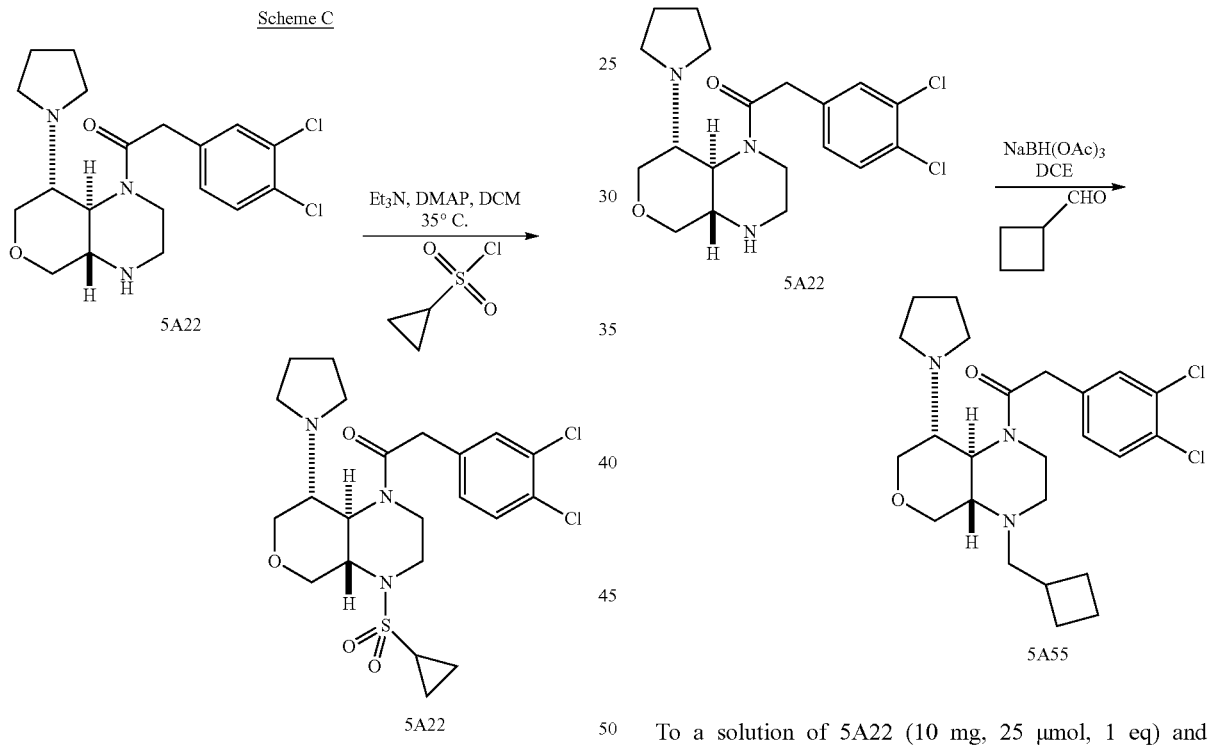

To a solution of 5A22 (100 mg, 250 μmol, 1 eq) in DCM (3 mL) was added Et$_3$N (127 mg, 1.26 mmol, 175 μL, 5 eq), DMAP (3.1 mg, 25 μmol, 0.1 eq) and cyclopropanesulfonyl chloride (71 mg, 500 μmol, 2 eq). The mixture was stirred at 35° C. for 12 hours under N$_2$. The reaction mixture was concentrated under reduced pressure to give a residue. The residue was purified by preparative-HPLC (column: Waters Xbridge Prep OBD C18 150×30 mm, 10 micron; mobile phase: [water(0.1% TFA)-ACN]; ACN %: 10%-70%, 10 min). to provide 5A22 as an off-white solid. $^1$H NMR (methanol-d$_4$, TFA salt, 400 MHz) δ 7.48-7.53 (m, 2H), 7.25 (dd, J=8.25, 2.02 Hz, 1H), 4.30-4.45 (m, 2H), 4.16-4.29 (m, 2H), 3.88-4.00 (m, 4H), 3.74-3.87 (m, 3H), 3.47-3.71 (m, 4H), 3.36-3.42 (m, 2H), 2.43-2.55 (m, 1H), 1.88-2.16 (m, 4H), 0.95-1.16 (m, 4H). LCMS (MH$^+$) 502.1.

To a solution of 5A22 (10 mg, 25 μmol, 1 eq) and cyclobutane carbaldehyde (4.22 mg, 50 μmol, 2 eq) in DCE (2 mL) was added (CH$_3$COO)$_3$BHNa (11 mg, 50 μmol, 2.00 eq). The resulting mixture was stirred at 20° C. under N$_2$ for 12 hrs. The reaction mixture was concentrated under reduced pressure to remove solvent. The residue was purified by preparative-HPLC (TFA condition: column: Waters Xbridge Prep OBD C18 150×30 mm, 10 μm; mobile phase: [water (0.1% TFA)-ACN]; ACN %: 10%-70%, 10 min) which provided 5A55 as the TFA salt. 1H NMR (400 MHz, TFA salt, methanol-d$_4$) δ=7.56-7.46 (m, 2H), 7.26 (dd, J=1.7, 8.2 Hz, 1H), 4.72 (dt, J=4.8, 10.2 Hz, 1H), 4.42 (dd, J=4.8, 10.6 Hz, 1H), 4.33 (dd, J=4.5, 11.7 Hz, 1H), 4.28-4.14 (m, 2H), 3.89 (s, 2H), 3.86-3.75 (m, 1H), 3.69-3.58 (m, 3H), 3.58-3.44 (m, 4H), 3.15 (br dd, J=6.5, 12.8 Hz, 1H), 3.00-2.88 (m, 2H), 2.69 (td, J=7.5, 15.0 Hz, 1H), 2.21-1.94 (m, 7H), 1.91-1.75 (m, 3H). LCMS (MH$^+$) 466.1.

TABLE B

| Example | Structure | Reagent Scheme D | Data 1H NMR (400 MHz) | LCMS |
|---|---|---|---|---|
| 5A54 | 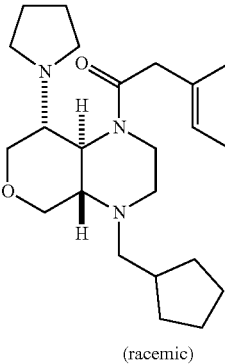<br>(racemic) | CHO with cyclopentyl | (TFA salt, methanol-d₄) δ = 7.55-7.46 (m, 2H), 7.26 (dd, J = 1.8, 8.3 Hz, 1H), 4.67 (dt, J = 4.8, 10.1 Hz, 1H), 4.39-4.28 (m, 2H), 4.18-4.02 (m 2H), 3.88 (s, 2H), 3.71 (br d, J = 14.5 Hz, 1H), 3.67-3.58 (m, 2H), 3.58-3.47 (m, 2H), 3.37 (br d, J = 18.2 Hz, 2H), 3.14 (br d, J = 1.6 Hz, 1H), 2.84-2.64 (m, 3H), 2.16-1.94 (m, 5H), 1.81 (br s, 2H), 1.72-1.54 (m, 4H), 1.28-1.12 (m, 2H) | (MH+) 480.2 |
| 5A70 | 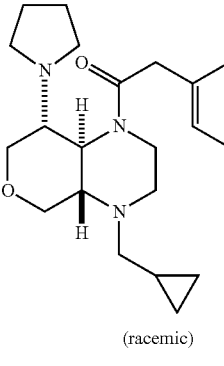<br>(racemic) | CHO with cyclopropyl | (400 MHz, TFA salt, chloroform-d) δ = 7.47-7.41 (m, 2H), 7.19 (br d, J = 8.1 Hz, 1H), 4.95 (br s, 1H), 4.51 (br s, 1H), 4.28-4.14 (m, 2H), 4.06 (br d, J = 14.5 Hz, 1H), 3.91-3.75 (m, 4H), 3.73-3.63 (m, 3H), 3.60 (br d, J = 10.3 Hz, 2H), 3.47 (br s, 1H), 2.83-2.75 (m, 1H), 2.75-2.56 (m, 2H), 2.02 (br s, 4H), 0.89 (br s, 1H), 0.80-0.65 (m, 2H), 0.32-0.19 (m, 2H) | (MH+) 452.2 |
| 5A71 | 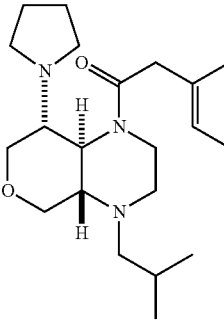<br>(racemic) | CHO with isopropyl | (TFA salt, chloroform-d) δ = 7.52-7.46 (m, 2H), 7.24 (dd, J = 2.0, 8.2 Hz, 1H), 4.67 (dt, J = 4.5, 10.2 Hz, 1H), 4.32 (ddd, J = 4.7, 11.4, 19.4 Hz, 2H), 4.16-4.06 (m, 2H), 3.87 (d, J = 2.2 Hz, 2H), 3.78-3.68 (m, 1H), 3.62 (br dd, J = 9.9, 11.5 Hz, 2H), 3.52 (br t, J = 10.7 Hz, 2H), 3.39 (br d, J = 12.3 Hz, 2H), 3.27-3.21 (m, 1H), 2.77 (br s, 1H), 2.69-2.60 (m, 1H), 2.51 (br dd, J = 4.2, 12.1 Hz, 1H), 2.02 (br s, 4H), 1.94-1.83 (m, 1H), 0.95 (dd, J = 2.9, 6.6 Hz, 6H) | (MH+) 454.1 |
| 5A72 | 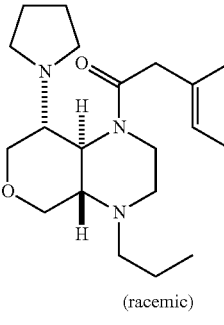<br>(racemic) | CHO with ethyl | (chloroform-d) δ = 7.42-7.34 (m, 2H), 7.14 (dd, J = 1.9, 8.3 Hz, 1H), 4.18 (dd, J = 4.8, 11.2 Hz, 1H), 4.09 (br s, 1H), 3.76 (br d, J = 15.3 Hz, 2H), 3.68-3.58 (m, 1H), 3.34-3.03 (m, 3H), 2.90 (br d, J = 9.7 Hz, 1H), 2.71 (br s, 3H), 2.52-2.42 (m, 1H), 2.31-2.18 (m, 2H), 1.72 (br s, 1H), 1.58 (br s, 6H), 1.48-1.33 (m, 2H), 0.85 (t, J = 7.3 Hz, 3H) | (MH+) 440.3 |

ROCK-5A67 is made as shown in Scheme E:

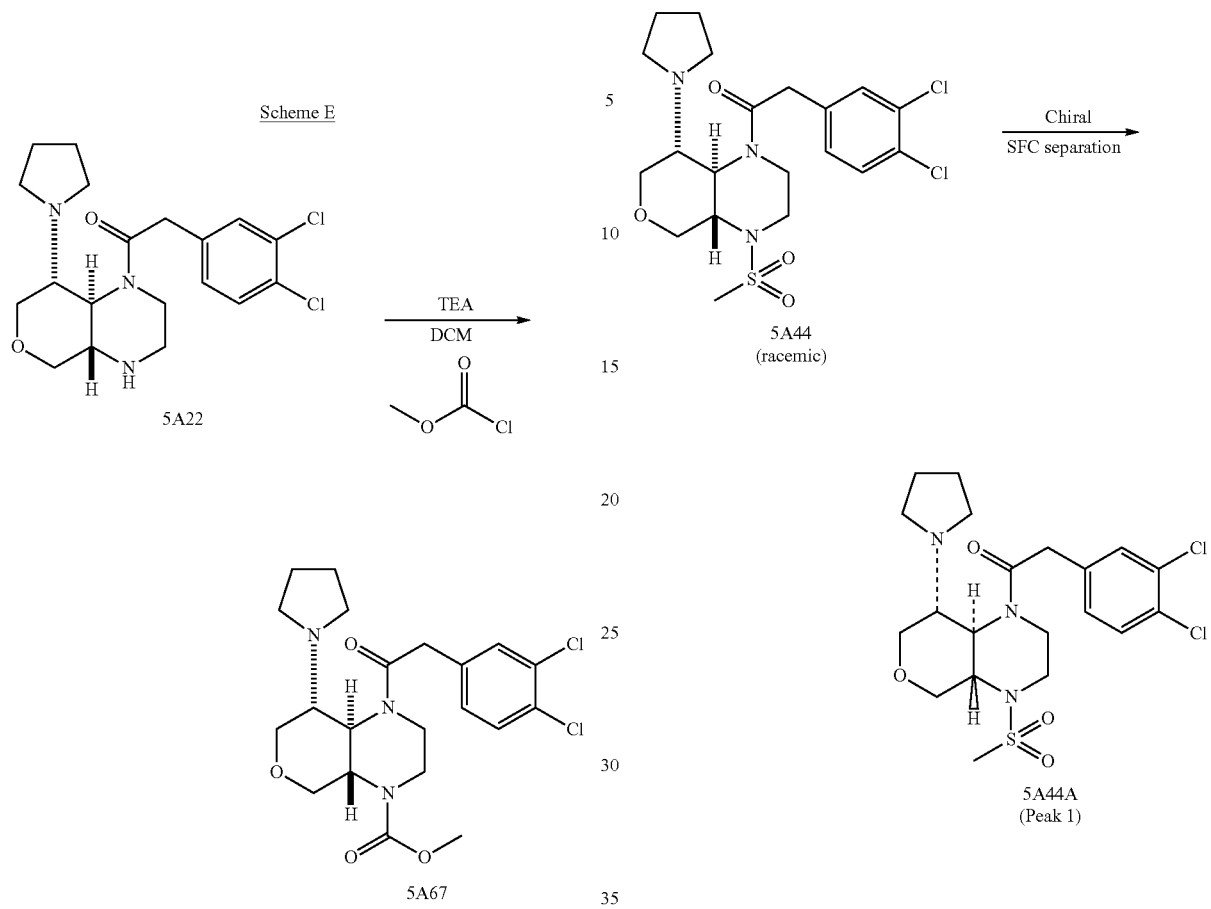

5A22 (5 mg, 12 μmol, 1 eq) and TEA (13 mg, 125 μmol, 18 μL, 10 eq) were dissolved in DCM (1 mL). Methylchloroformate (2.4 mg, 25 μmol, 1.94 μL, 2 eq) was added. The resulting mixture was stirred at 20° C. under $N_2$ for 12 hrs. The reaction mixture was concentrated under reduced pressure. The residue was purified by preparative-HPLC (TFA condition: column: Luna C18 100×30 mm, 5 micron; mobile phase: [water (0.1% TFA)-ACN]; ACN %: 15%-45%, 10 min) which provided 5A67 as the TFA salt. 1H NMR (400 MHz, TFA salt, chloroform-d) δ=7.34 (d, J=8.2 Hz, 1H), 7.25 (d, J=1.7 Hz, 1H), 6.99 (dd, J=1.6, 8.2 Hz, 1H), 5.59 (br s, 1H), 4.50 (br s, 1H), 4.20-4.04 (m, 3H), 3.92 (br d, J=7.6 Hz, 2H), 3.73 (br d, J=5.9 Hz, 4H), 3.57 (s, 5H), 3.39 (br s, 1H), 3.22 (br s, 1H), 3.02-2.79 (m, 2H), 1.93 (br s, 4H). LCMS (MH+) 456.1.

The preparation of enantiomers ROCK-5A44A and 5A44B via chiral separation is shown in Scheme F. Absolute stereochemistry is undetermined. Enantiomers are characterized by order of elution under the conditions shown.

Racemic-5A44 was separated by chiral SFC (column: DAICEL CHIRALPAK ADH (250 mm×30 mm, 5 μm); mobile phase: [Neutral-IPA]; IPA %: 45%-45%, 15 min) which provided 5A44A (Peak 1: retention time—2.4 minutes) and 5A44B (Peak 2: retention time—3.02 minutes).

The preparation of enantiomers ROCK-5A52A and 5A52B via chiral separation is shown in Scheme G. Absolute stereochemistry is undetermined. Enantiomers are characterized by order of elution under the conditions shown.

Scheme G

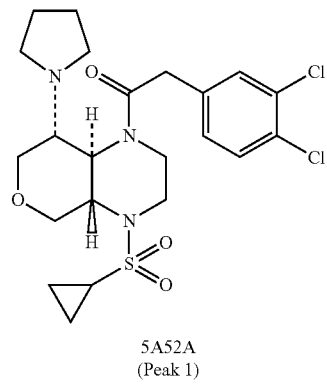

5A52A
(Peak 1)

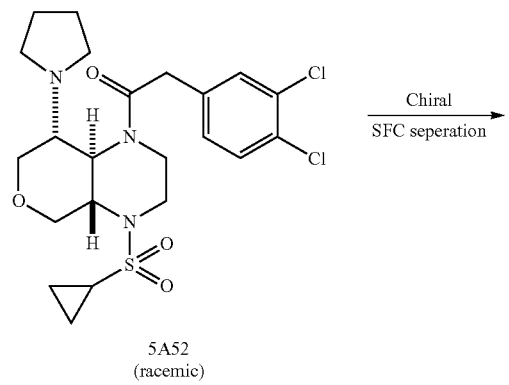

5A52
(racemic)

Chiral SFC seperation →

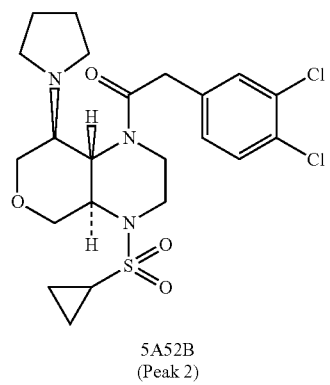

5A52B
(Peak 2)

Racemic 5A52 was separated by SFC (column: DAICEL CHIRALCEL OD-H (250 mm×30 mm, 5 μm); mobile phase: [0.1% NH$_3$H$_2$O EtOH]; EtOH %: 30%-30%, 7 min) which provided 5A52A (Peak 1-2.02 minutes) and 5A52B (Peak 2-2.33 minutes).

The preparation of enantiomers ROCK-5A24A and 5A24B via chiral separation is shown in Scheme H. Absolute stereochemistry is undetermined. Enantiomers are characterized by order of elution under the conditions shown.

Scheme H

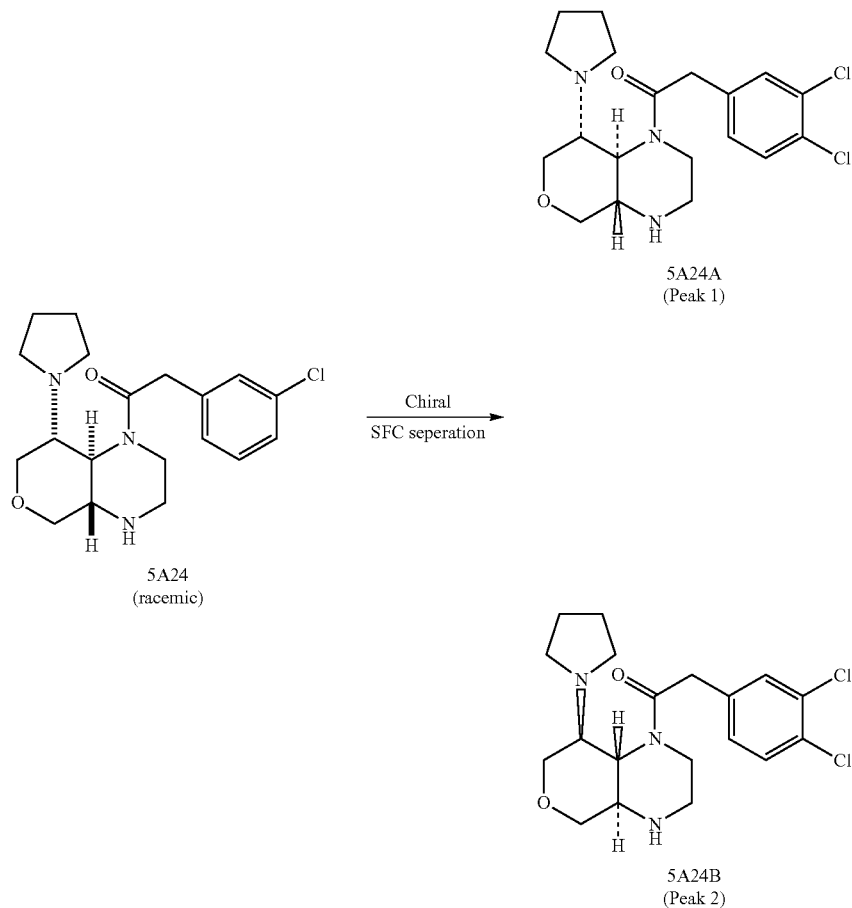

Racemic 5A24 was separated by SFC (column: DAICEL CHIRALPAK AD-H (250 mm×30 mm, 5 μm); mobile phase: [Neutral-IPA]; IPA %: 24%-24%, 6 min) which provided 5A24A (Peak 1-1.93 minutes) and 5A24B (Peak 2-2.21 minutes).

The preparation of enantiomers ROCK-5A53A and 5A53B via chiral separation is shown in Scheme I. Absolute stereochemistry is undetermined. Enantiomers are characterized by order of elution under the conditions shown.

Scheme I

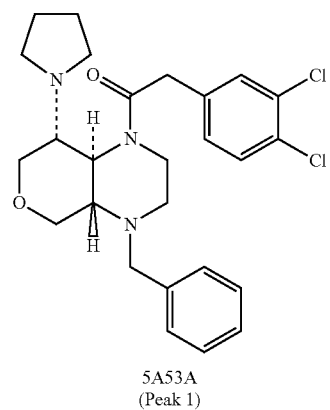

5A53A
(Peak 1)

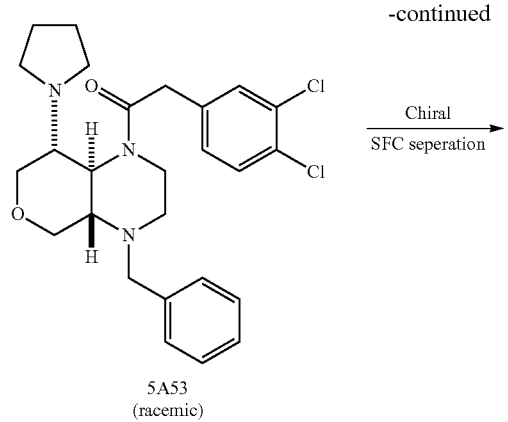

5A53
(racemic)

-continued

Chiral SFC seperation →

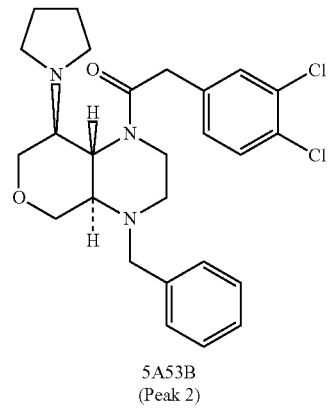

5A53B
(Peak 2)

Racemic 5A53 was separated by SFC (column: DAICEL CHIRALCEL OJ (250 mm×50 mm, 10 μm); mobile phase: [0.1% NH$_3$H$_2$O IPA]; IPA %: 40%-40%, 6.2 min) which provided 5A53A (Peak 1-1.55 minutes) and 5A53B (Peak 2-1.73 minutes). Peak 1 (5A53) was further purified by prep-HPLC (column: Kromasil 250×50 mm, 10 μm; mobile phase: [water (10 mM NH$_4$HCO$_3$)-ACN]; ACN %: 50%-80%, 10 min).

The preparation of enantiomers ROCK-5A55A and 5A55B via chiral separation is shown in Scheme J. Absolute stereochemistry is undetermined. Enantiomers are characterized by order of elution under the conditions shown.

Scheme J

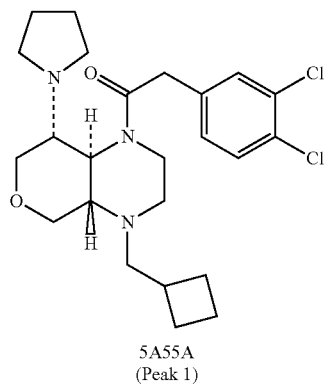

5A55A
(Peak 1)

-continued
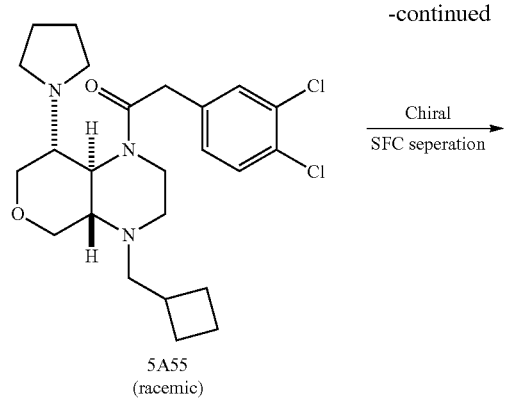
5A55
(racemic)
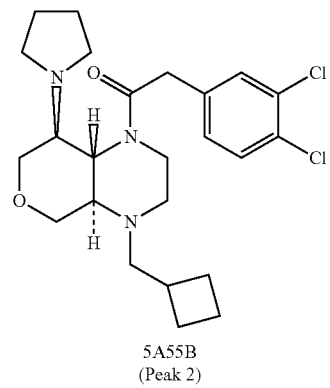
5A55B
(Peak 2)
Racemic 5A55 was separated by SFC (column: DAICEL CHIRALPAK AD-H (250 mm×30 mm, 5 µm); mobile phase: [0.1% NH$_3$H$_2$O EtOH]; EtOH %: 38%-38%, 7 min) which provided 5A55A (Peak 1-1.99 minutes) and 5A55B (Peak 2-2.08 minutes).
ROCK-5A50 is made as shown in Scheme K:
Scheme K
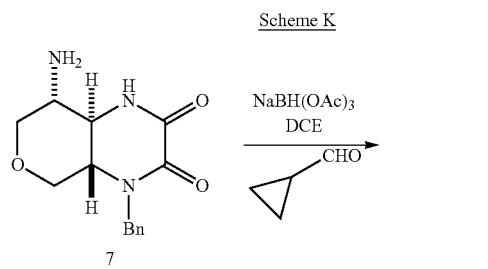
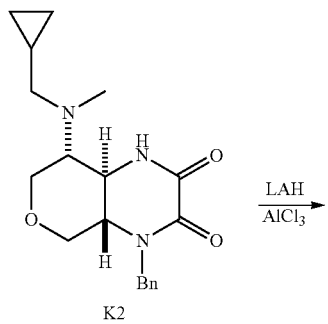
-continued
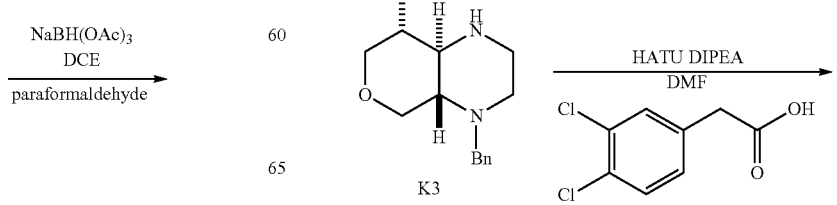

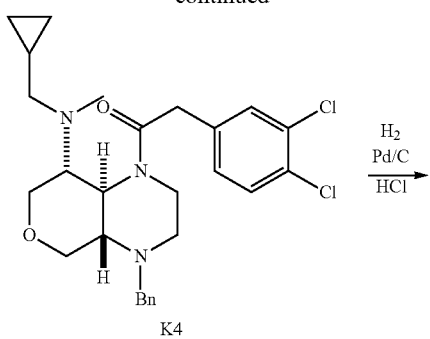

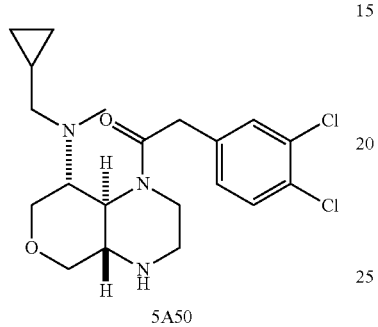

Example Experimentals for Scheme K:

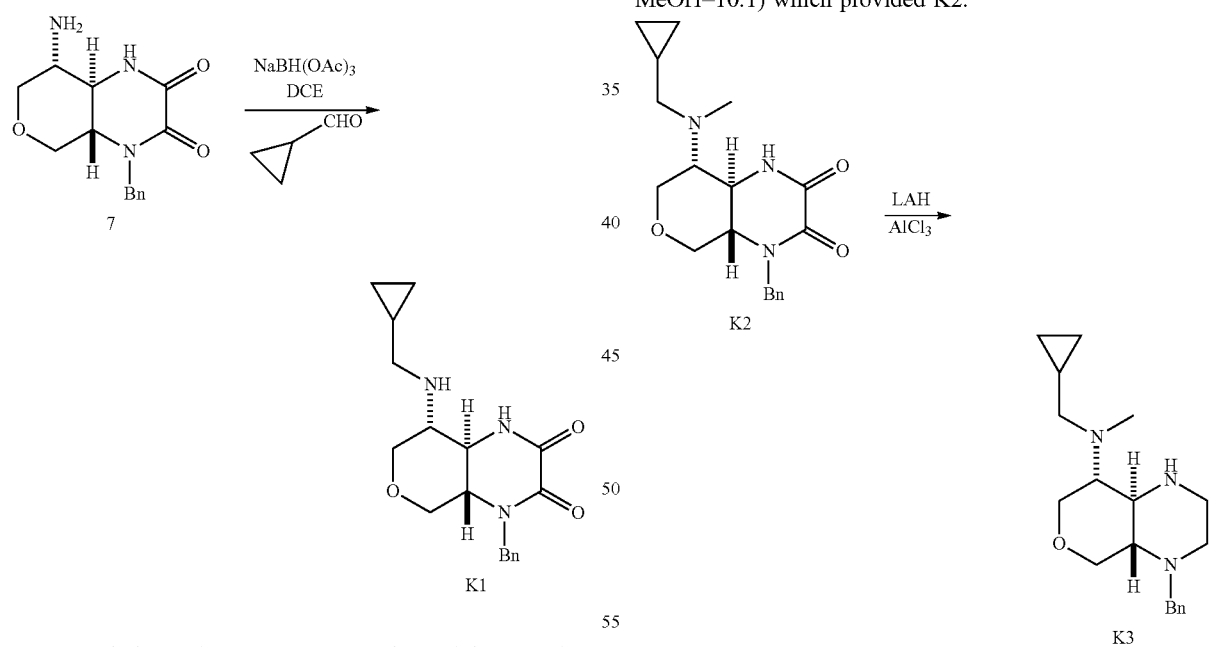

To a solution 7 (500 mg, 1.82 mmol, 1 eq) in DCE (20 mL) was added cyclopropanecarbaldehyde (127 mg, 1.82 mmol, 135 uL, 1 eq). The mixture was degassed and purged with N$_2$ (3 times). The mixture was stirred at 20° C. for 12 hrs under a N$_2$ atmosphere.

After 12 hrs, NaBH(OAc)$_3$ (770 mg, 3.63 mmol, 2 eq) was added. The mixture was stirred at 20° C. for 12 hrs under a N$_2$ atmosphere. The reaction mixture was concentrated under reduced pressure. The residue was purified by prep-TLC (SiO2, DCM:MeOH=10:1) which provided K1.

To a solution K1 (30 mg, 91 μmol, 1 eq) in DCE (10 mL) was added NaBH(OAc)$_3$ (58 mg, 270 μmol, 3 eq) and paraformaldehyde (100 mg, 2.91 mmol, 32 eq). The mixture was stirred at 20° C. for 12 hrs under a N$_2$ atmosphere. The reaction mixture was concentrated under reduced pressure. The residue was purified by preparative-TLC (SiO$_2$, DCM:MeOH=10:1) which provided K2.

To a solution AlCl$_3$ (105 mg, 786 μmol, 43 μL, 2.7 eq) in THF (20 mL) was added LiAlH$_4$ (90 mg, 2.4 mmol, 8.1 eq) at 0° C. The resulting mixture was stirred at 20° C. for 0.5 hr. A solution of K2 (100 mg, 291 μmol, 1 eq) in THF (20 mL) was added to the reaction mixture at 0° C. The resulting mixture was stirred at 0° C. (1 hr) and then allowed to warm to 20° C. (6 hrs). The reaction mixture was quenched with 2 N NaOH$_{(aq.)}$ (30 mL) at 0° C. The mixture was filtered, and the filtrate was concentrated to give a residue. The residue was diluted with EtOAc (50 mL), dried over sodium sulfate, and concentrated. The residue was purified by preparative-HPLC (TFA condition: column: Nano-micro Kromasil C18

100×30 mm, 5 µm; mobile phase: [water (0.1% TFA)-ACN]; ACN %: 8%-28%, 10 min) which provided K3.

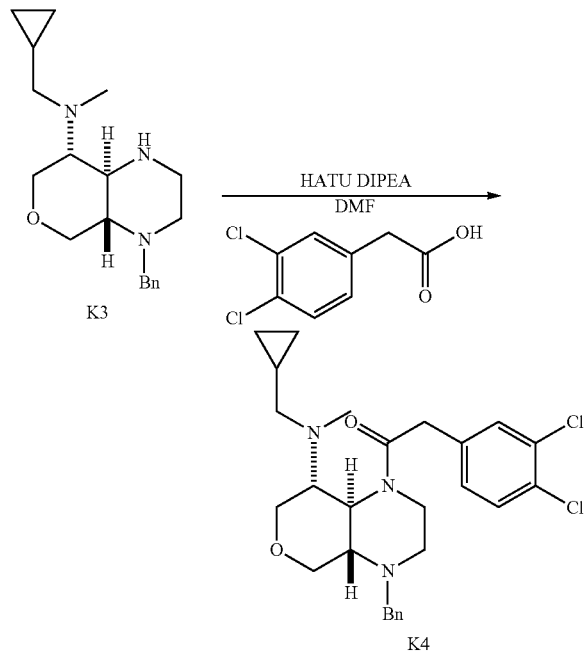

The amine K3 (39 mg, 190 µmol, 1.2 eq), DIPEA (82 mg, 634 µmol, 110 µL, 4 eq) and HATU (72 mg, 190 µmol, 1.2 eq) were dissolved in DMF (3 mL). 2-(3,4-Dichlorophenyl) acetic acid (50 mg, 159 µmol, 1 eq) was added. The resulting mixture was stirred at 20° C. for 12 hrs. The reaction mixture was concentrated under reduced pressure to remove solvent. The residue was purified by preparative-HPLC (TFA condition: column: Nano-Micro UniSil 5-100 C18 ULTRA 100×250 mm, 5 µm; mobile phase: [water (0.1% TFA)-ACN]; ACN %: 25%-55%, 11 min) which provided K4.

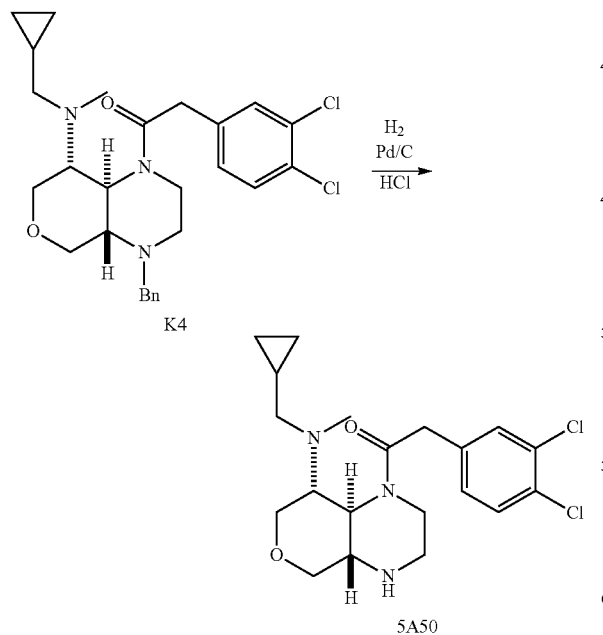

A solution of K4 (40 mg, 80 µmol, 1 eq), Pd/C (5.5 mg, 80 µmol, 10 wt % Pd, 1 eq) in THF/H$_2$O/HCl (2 mL, 2 mL, 0.4 mL) was stirred at 20° C. under H$_2$ (15 psi) for 6 hrs. The mixture was filtered through a pad of Celite, and the filtrate was concentrated. The residue was purified by preparative-HPLC (TFA condition: column: Waters Xbridge 150×25 mm, 5 micron; mobile phase: [water (0.1% TFA)-ACN]; ACN %: 10%-40%, 12 min) which provided 5A50. 1H NMR (400 MHz, TFA salt, methanol-d$_4$) δ=7.54-7.47 (m, 2H), 7.24 (dd, J=2.0, 8.2 Hz, 1H), 4.71 (br s, 1H), 4.36 (br dd, J=3.9, 11.6 Hz, 2H), 4.31-4.16 (m, 2H), 4.10 (br dd, J=4.8, 11.1 Hz, 1H), 3.90 (s, 2H), 3.68 (br s, 3H), 3.59-3.42 (m, 2H), 3.36-3.33 (m, 1H), 3.27-3.19 (m, 1H), 3.17-3.06 (m, 1H), 2.97 (br s, 2H), 1.12 (br s, 1H), 0.74 (br d, J=6.5 Hz, 2H), 0.41 (br s, 2H). LCMS (MH$^+$) 412.1.

ROCK-5A51 is made as shown in Scheme L:

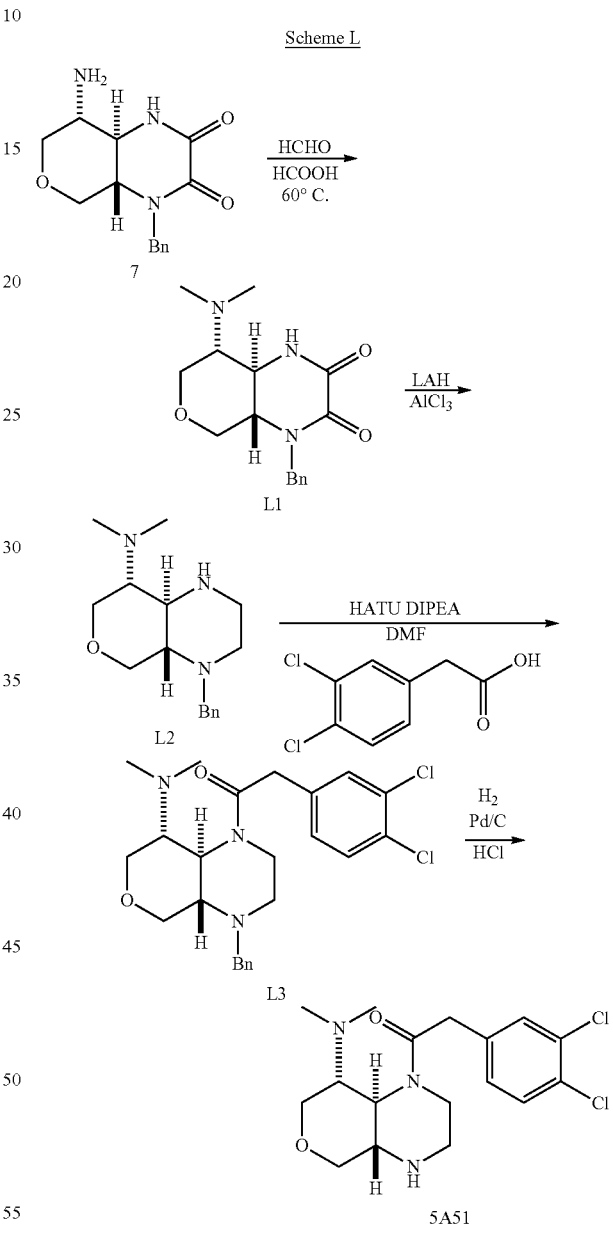

Example Experimentals for Scheme L:

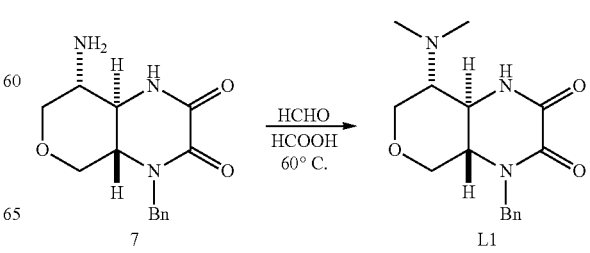

To a solution 7 (200 mg, 726 μmol, 1 eq) in HCOOH (20 mL) was added HCHO (1.89 g, 23 mmol, 1.73 mL, 37% purity, 32 eq). The mixture was stirred at 60° C. for 12 hours under a $N_2$ atmosphere. The reaction mixture was concentrated under reduced pressure to remove solvent. The residue was purified by prep-TLC ($SiO_2$, DCM:MeOH=10:1) which furnished L1.

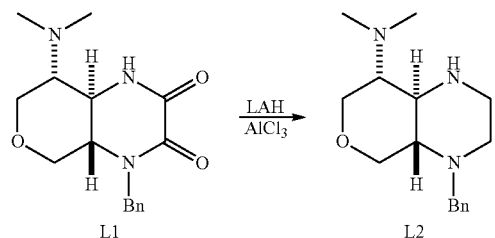

To a solution $AlCl_3$ (154 mg, 1.16 mmol, 63 μL, 2.7 eq) in TH (20 mL) was added $LiAlH_4$ (132 mg, 3.47 mmol, 8.1 eq) at 0° C. The resulting mixture was stirred at 20° C. for 0.5 hr. A solution of L1 in THE (20 mL) was added to the mixture at 0° C. The mixture was stirred at 0° C. for 1 hr and then at 20° C. for 6 hours. The reaction mixture was quenched with 2N $NaOH_{(aq.)}$ (30 mL) at 0° C. The mixture was filtered, and the filtrate was concentrated. The residue was diluted with EtOAc (50 mL), dried over sodium sulfate, filtered, and concentrated. The residue was purified by preparative-HPLC (TFA condition: column: Nano-micro Kromasil C18 100×30 mm, 5 μm; mobile phase: [water (0.1% TFA)-ACN]; ACN %: 5%-25%, 10 min) which provided L2.

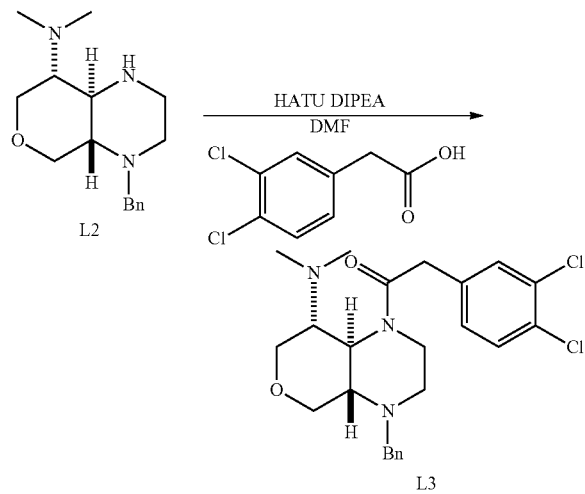

The amine L2 (107 mg, 523 μmol, 1.2 eq), DIPEA (225 mg, 1.74 mmol, 304 μL, 4 eq) and HATU (199 mg, 523 μmol, 1.2 eq) were dissolved in DMF (3 mL). 2-(3,4-Dichlorophenyl)acetic acid (120 mg, 436 μmol, 1 eq) was added. The mixture was stirred at 20° C. for 12 hrs. The reaction mixture was concentrated under reduced pressure to remove solvent. The residue was purified by preparative-HPLC (basic condition: column: Waters Xbridge 150×25 mm, 5 μM; mobile phase: [water (0.04% $NH_3H_2O$+10 mM $NH_4HCO_3$)-ACN]; ACN %: 45%-75%, 10 min). which provided L3.

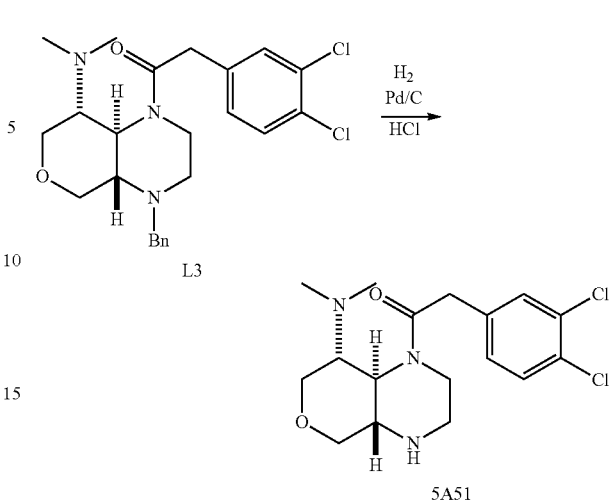

A solution of L3 (15 mg, 32 μmol, 1 eq) and Pd/C (2 mg, 10 wt % Pd) in THF/HCl/$H_2O$ (2 mL 0.4 mL/2 mL) was stirred at 20° C. under $H_2$ (15 psi) for 6 hours. The mixture was filtered through a plug of Celite, and the filtrate was concentrated under reduced pressure to remove solvent. The residue was purified by preparative-HPLC (TFA condition: column: Luna C18 100×30 mm, 5 μm; mobile phase: [water (0.1% TFA)-ACN]; ACN %: 1%-30%, 10 min) which provided 5A50. 1H NMR (400 MHz, TFA salt, methanol-$d_4$) δ=7.53-7.47 (m, 2H), 7.24 (dd, J=2.0, 8.2 Hz, 1H), 4.64 (dt, J=4.2, 10.8 Hz, 1H), 4.42 (dd, J=4.2, 11.5 Hz, 1H), 4.33-4.18 (m, 2H), 4.11 (dd, J=5.0, 11.0 Hz, 1H), 3.94-3.83 (m, 2H), 3.79-3.60 (m, 3H), 3.58-3.44 (m, 2H), 3.29-3.21 (m, 1H), 2.95 (br s, 6H). LCMS (MH+) 372.1.

Compounds of the invention may be tested in the following screens

Tritiated U69,593 binding for KOP-R membranes; tritiated DAMGO binding for MOP-R membranes; and tritiated DPDPE binding for DOP-R membranes:

Membranes from cells stably expressing kappa, mu or delta opioid receptor constructs (PathHunter U2OS hOPRK1, CHO-K1 rOPRM1 and CHO-K1 OPRD1 β-arrestin cell line, DiscoverX, Fremont, Calif., USA) were used. Cells were scraped from tissue culture plates, homogenized with a tissue tearor homogenizer in membrane buffer (10 mM Tris, 100 mM NaCl, and 1 mM EDTA; pH 7.4), and centrifuged at 20,000 g for 30 minutes at 4° C. and frozen at −80° C. until use. Prior to use, the pellets were resuspended in binding buffer (50 mm Tris, 100 mm NaCl, pH 7.4), homogenized with a dounce homogenizer and 50 g incubated with 1.0 nM of the appropriate tritiated ligand ([$^3$H]U69,593, [$^3$H]DAMGO or [$^3$H]DPDPE for kappa, mu or delta binding, respectively) and the appropriate concentration of compound for 60 minutes at 30° C. Membranes with bound tritiated ligand were collected on Whatman GF/B filter paper (Brandel, Gaithersburg, Md., USA) utilizing a Brandel harvester. Bound tritiated ligand was quantified using a TriCarb-2900TR scintillation counter (Packard, Downers Grove, Ill., USA) following addition of 4 ml ReadySafe scintillation fluid (Beckman Coulter, Indianapolis, Ind., USA). Compiled data for each compound was normalized to the maximal binding in the absence of compound, with non-specific binding subtracted. Curve fitting was done in Microcal Origin 17.0 software using logistic sigmoidal fit, to determine $IC_{50}$.

GTPgammaS
Membranes from U2OS cells stably expressing human kappa opioid receptors were used. Cells were scraped from tissue culture plates, homogenized with a tissue tearor homogenizer in membrane buffer (10 mM Tris, 100 mM NaCl, and 1 mM EDTA; pH 7.4), and centrifuged at 20,000 g for 30 minutes at 4° C. and frozen at −80° C. until use. Prior to use, the pellets were resuspended in assay buffer (50 mm Tris, 100 mm NaCl, 5 mM $MgCl_2$, and 1 mM EDTA; pH 7.4) and homogenized with a dounce homogenizer and 50 µg incubated with 0.1 nM [35 S]GTPγS, 10 nM GDP, and the appropriate concentration of agonist for 20 minutes at 30° C. To test inhibition, all samples were incubated with 100 nM U69,593 as well as the appropriate concentration of compound. Membranes with bound [35 S]GTPγS were collected on Whatman GF/B filter paper (Brandel, Gaithersburg, Md., USA) utilizing a Brandel harvester. Bound [35 S]GTPγS was quantified using a TriCarb-2900TR scintillation counter (Packard, Downers Grove, Ill., USA) following addition of 4 mL ReadySafe scintillation fluid (Beckman Coulter, Indianapolis, Ind., USA). "No Stim" indicates that there was no stimulation in this assay, at the highest dose tested, 10,000 nM. NA indicates not applicable. For each compound, curve fitting was done in Microcal Origin 17.0 software using logistic sigmoidal fit, to determine $EC_{50}$ and maximal percent stimulation, which in turn was normalized to the maximal percent stimulation of the test full agonist compound U69,593 to determine % efficacy.

$β_2$-Arrestin
Experiments were conducted using the PathHunter Detection Kit obtained from DiscoverX. Cells stably expressing kappa, mu or delta opioid receptor constructs (PathHunter U2OS hOPRK1, CHO-K1 rOPRM1 and CHO-K1 OPRD1 β-arrestin cell line, DiscoverX, Fremont, Calif., USA) were plated in 96- or 384-well plates. Cells were stimulated with the compounds for 90 minutes at 37° C. To test inhibition, all samples were incubated with 100 nM U69,593 as well as the appropriate concentration of compound. Cells were then incubated for 60 minutes in the presence of galoctosidase substrate, yielding chemiluminescent product. Chemiluminescence was measured using a Synergy Neo microplate reader (BioTek, Winooski, Vt., USA). Antagonism assays were done in the same manner, in the presence of 300 nM U69,593, 1 µM DAMGO or 1 µM DPDPE for KOP-R, MOP-R or DOP-R assays, respectively. "No Stim" indicates that there was no stimulation in this assay, at the highest dose tested, 10,000 nM. NA indicates not applicable. For each compound, curve fitting was done in Microcal Origin 17.0 software using logistic sigmoidal fit, to determine $EC_{50}$ and maximal percent stimulation, which in turn was normalized to the maximal percent stimulation of the test full agonist compound U69,593 to determine % efficacy.

Representative compounds of the invention were tested in the foregoing screens with the following results:

TABLE A

| | | Stimulation data | | | | |
| --- | --- | --- | --- | --- | --- | --- |
| | | | GTPγS stimulation | | β-arrestin coupling | |
| Example | Structure | Binding $IC_{50}$ (nM) | $EC_{50}$ (nM) | % efficacy | $EC_{50}$ (nM) | % efficacy |
| 5A22 | (racemic) | 65 | 63 | 96 | 1132 | 67 |
| 5A23 | (racemic) | 103 | 46 | 76 | 5540 | 44 |

TABLE A-continued
| | | | GTPγS stimulation | | β-arrestin coupling | |
|---|---|---|---|---|---|---|
| Example | Structure | Binding $IC_{50}$ (nM) | $EC_{50}$ (nM) | % efficacy | $EC_{50}$ (nM) | % efficacy |
| 5A25 | 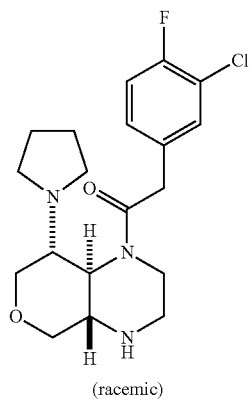 [SMILES: O=C(Cc1ccc(F)c(Cl)c1)N1CCN[C@@H]2COC[C@H](N3CCCC3)[C@H]21] (racemic) | 249 | 571 | 93 | 13600 | 29 |
| 5A26 | 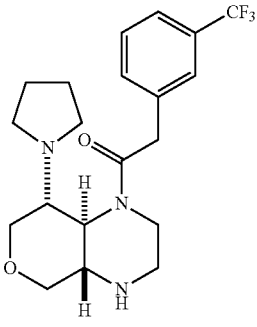 (racemic) | 112 | 130 | 108 | 3260 | 42 |
| 5A32 | 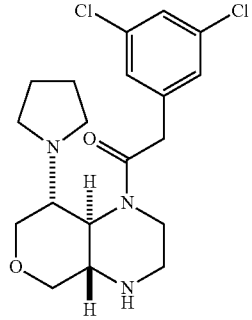 (racemic) | 410 | 464 | 66.5 | No stim | No stim |

TABLE A-continued
Stimulation data
| Example | Structure | Binding IC$_{50}$ (nM) | GTPγS stimulation | | β-arrestin coupling | |
|---|---|---|---|---|---|---|
| | | | EC$_{50}$ (nM) | % efficacy | EC$_{50}$ (nM) | % efficacy |
| 5A40 | 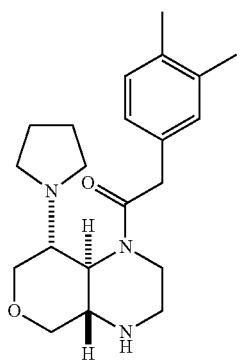 (racemic) | 719 | 1703 | 111 | No stim | No stim |
| 5A44 | 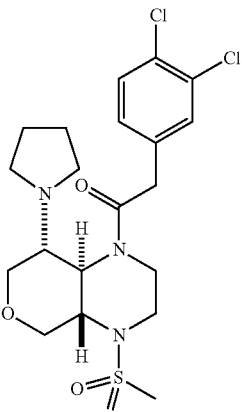 (racemic) | 19 | 6.7 | 88 | 6200 | 55 |
| 5A24 | 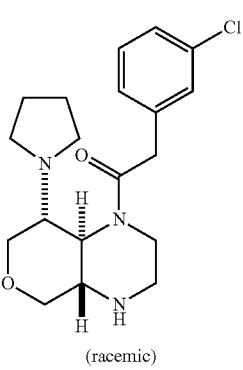 [SMILES: O=C(Cc1cccc(Cl)c1)N1CCN[C@@H]2COC[C@H](N3CCCC3)[C@H]21] (racemic) | 251 | 213 | 64 | NA | No stim |

TABLE A-continued
| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A46 | 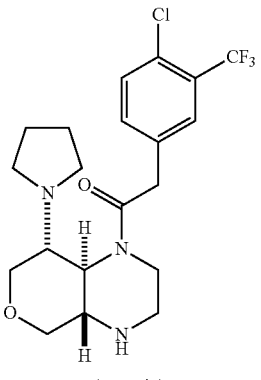 (racemic) | 15 | 6.3 | 131 | NA | 100% at 10 μM |
| 5A47 | 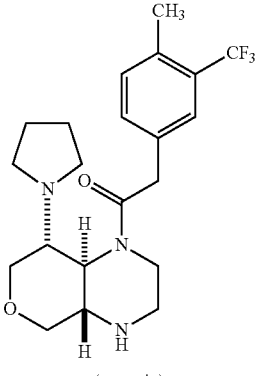 (racemic) | 31 | 9.0 | 84 | 4900 | 78 |
| 5A49 | 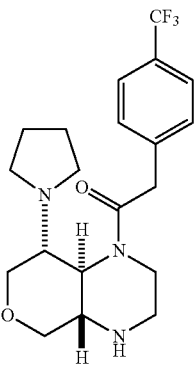 (racemic) | 102 | 109 | 69 | 11000 | 36 |

TABLE A-continued

| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A53 | (racemic) | 40 | 12 | 82 | NA | 80% at 10 μM |
| 5A52 | (racemic) | 5.1 | 3.0 | 101 | 3300 | 79 |
| 5A55 | (racemic) | 57 | 21 | 67 | NA | 40% at 10 μM |

TABLE A-continued
| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A54 | 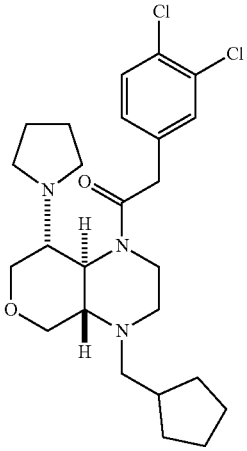 (racemic) | 73 | 31 | 73 | NA | 20% at 10 μM |
| 5A57 | 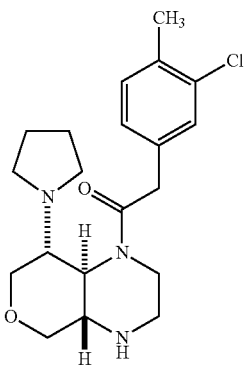 (racemic) | 42 | 62 | 98 | NA | 20% at 10 μM |
| 5A58 | 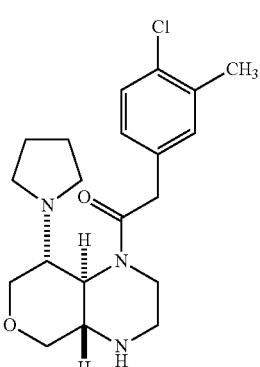 (racemic) | 116 | 261 | 161 | NA | 20% at 10 μM |

TABLE A-continued
| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A65 | 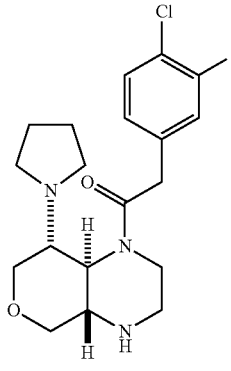 (racemic) | 68 | 136 | 121 | NA | 20% at 10 μM |
| 5A66 | 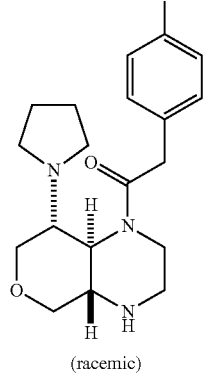 (racemic) | 456 | 566 | 140 | NA | 20% at 10 μM |
| 5A67 | 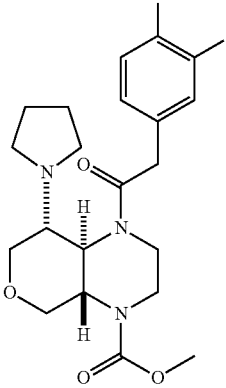 (racemic) | 41 | 12 | 85 | 5200 | 85 |

TABLE A-continued
| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A70 | 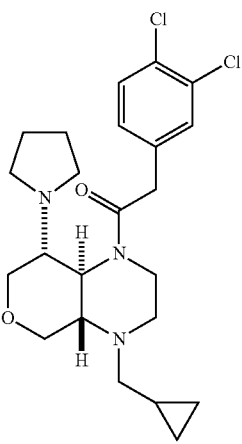<br>(racemic) | 71 | 19 | 90 | NA | 50% at 10 μM |
| 5A71 | 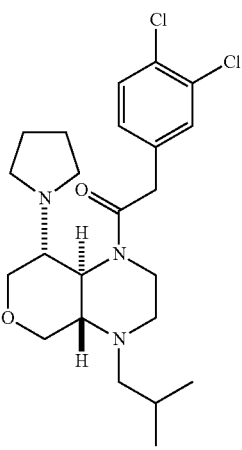<br>(racemic) | 27 | 14 | 93 | NA | 40% at 10 μM |
| 5A72 | 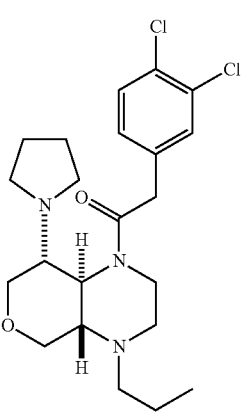<br>(racemic) | 26 | 12 | 111 | NA | 50% at 10 μM |

TABLE A-continued

| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A51 | (racemic) | 120 | 108 | 71 | NA | No stim |
| 5A50 | (racemic) | 297 | 93 | 79 | NA | No stim |
| 5A64 | (racemic) | 1917 | 2125 | 68 | NA | No stim |

TABLE A-continued
| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A48 | 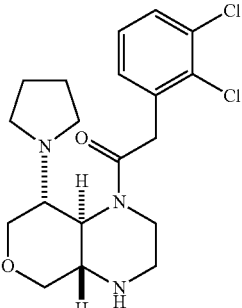 (racemic) | 1043 | 21788 | 181 | NA | No stim |
| 5A44A | 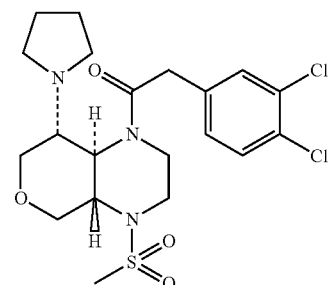 Peak 1 | 5.4 | 3.4 | 119 | NA | 80% at 10 µM |
| 5A44B | 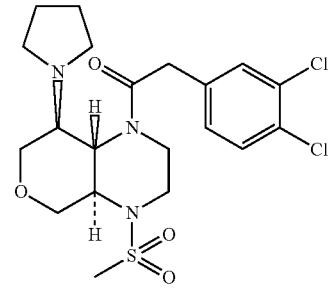 Peak 2 | 18 | 4.6 | 105 | NA | 70% at 10 µM |
| 5A52A | 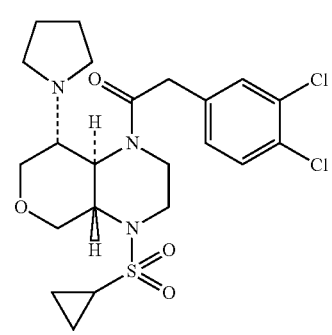 Peak 1 | 3.6 | 1.7 | 119 | NA | 60% at 10 µM |

TABLE A-continued

| | | | GTPγS stimulation | | β-arrestin coupling | |
|---|---|---|---|---|---|---|
| Example | Structure | Binding IC$_{50}$ (nM) | EC$_{50}$ (nM) | % efficacy | EC$_{50}$ (nM) | % efficacy |
| 5A52B | Peak 2 | 27 | 18 | 96 | NA | 25% at 10 μM |
| 5A24A | Peak 1 | 463 | 384 | 115 | NA | 0% at 10 μM |
| 5A24B | Peak 2 | 1125 | 1370 | 102 | NA | 0% at 10 μM |
| 5A53A | Peak 1 | 108 | 18 | 80 | NA | 80% at 10 μM |

TABLE A-continued

Stimulation data

| Example | Structure | Binding IC$_{50}$ (nM) | GTPγS stimulation | | β-arrestin coupling | |
|---|---|---|---|---|---|---|
| | | | EC$_{50}$ (nM) | % efficacy | EC$_{50}$ (nM) | % efficacy |
| 5A53B | Peak 2 | 44 | 4.8 | 58 | NA | 80% at 10 μM |
| 5A55A | Peak 1 | 94 | 30 | 84 | NA | No stim |
| 5A55B | Peak 2 | 20 | 13 | 62 | NA | 80% at 10 μM |

It has been demonstrated that prolactin release from the pituitary is a reliable biomarker of KOP-r agonism across species. Thus, demonstration of the release of prolactin by a compound which is predicted from in vitro GTPgammnaS assays in cell lines expressing KOP-r, in a manner blocked by a selective kappa antagonist, indicates an in vivo KOP-r agonistic effect. The demonstration of differential maximal efficacy in prolactin release compared to the full unbiased agonist U50488-induced release, coupled with submaximal kappa opioid receptor mediated GTPgammaS, indicates that the compound has in vivo partial agonist KOP-r activity.

In the case of rotarod incoordination, kappa agonist effects in this assay reflect kappa-opioid receptor arrestin mediated signaling. This assay is thought to be a sensitive measure of the sedative properties of kappa opioid receptor agonists. Generally, a compound which has reduced efficacy in the coupling of arrestin with the kappa opioid receptor is thought to have a lowered potential for the sedative side effects of kappa opioid receptor ligands. Rotarod assays in vivo are employed to confirm this possibility.

Prolactin

Mice were injected intraperitoneally with the compound to be tested 30 minutes prior to sampling. Trunk blood was collected by rapid decapitation, followed within 2 hours by preparation of serum. Serum prolactin levels were determined using a commercially available enzyme-linked immunoassay (AbCam, Cambridge, UK) following dilution of serum 5-fold in assay buffer. In this screen, compound 5A22 exhibited significant prolactin release at 5 mg/kg, and compound 5A23 exhibited significant prolactin release at 30 mg/kg.

Rotarod

Rotarod experiments were conducted with mice using a dedicated rodent rotarod apparatus, with up to five animals tested concurrently (IITC Life Science, Woodland Hills, Calif., USA). Rotarod rotation rate begins at 3 rotations per minute, and ramps to 30 rotations per minute over the course of 300 s, at which time the assay is terminated and animals removed to their home cage. Animals were acclimated to the rotarod on at least two occasions prior to the day of the test. On the day of the test, baseline times for each animal to fall off the rotarod were recorded. Mice were then injected intraperitoneally with vehicle or compound, and rotarod measurements conducted, beginning 0-2 minutes after injection, and then subsequently at select time points thereafter. Animals which failed to remain on the rotarod for at least 150 seconds during baseline testing were removed from the analysis. In this screen, compound 5A22 exhibited no significant incoordination at 10 mg/kg, but significant incoordination at 30 and 90 mg/kg, and compound 5A23 also exhibited no significant incoordination at 10 mg/kg but statistically significant incoordination at 30 and 90 mg/kg.

The invention claimed is:

1. A compound of Formula I

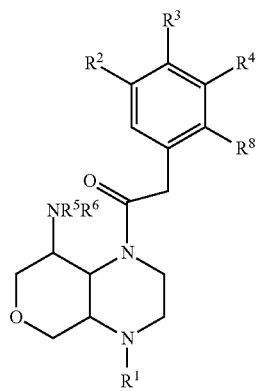

wherein
$R^1$ is chosen from hydrogen, $(C_1-C_{10})$hydrocarbyl, —C(=O)$(C_1-C_{10})$hydrocarbyl, —C(=O)O$(C_1-C_{10})$hydrocarbyl and —SO$_2$$(C_1-C_{10})$hydrocarbyl;
$R^2$, $R^3$, $R^4$, and $R^8$ are chosen independently from hydrogen, halogen, $(C_1-C_4)$alkyl, fluoro$(C_1-C_4)$alkyl, nitro, —SO$_3$H and —N$^+$HR$^5$R$^6$; with the provisos that (1) at least one of $R^2$, $R^3$, $R^4$, and $R^8$ must be other than hydrogen; and (2) when $R^2$ or $R^4$ is fluorine, at least one of the remaining substituents on phenyl must be other than hydrogen; and
$R^5$ and $R^6$ are chosen from $(C_1-C_{10})$hydrocarbyl, optionally substituted with fluoro, or, taken together with the nitrogen to which they are attached, $R^5$ and $R^6$ form a five-, six- or seven-membered non-aromatic heterocycle, which may be optionally substituted with fluoro or $(C_1-C_4)$alkyl.

2. A compound according to claim 1 wherein $R^8$ is hydrogen and one of $R^2$, $R^3$, and $R^4$ is hydrogen and the remaining two are chosen from hydrogen, halogen, fluoro $(C_1-C_4)$alkyl, and $(C_1-C_3)$alkyl.

3. A compound according to claim 2 wherein two of $R^2$, $R^3$, and $R^4$ are hydrogen and the remaining one is chosen from chloro, fluoro, trifluoromethyl, and methyl.

4. A compound according to claim 2 wherein $R^1$ is hydrogen.

5. A compound according to claim 2 wherein $R^1$ is chosen from $(C_1-C_7)$hydrocarbyl and —SO$_2$$(C_1-C_8)$hydrocarbyl.

6. A compound according to claim 5 wherein $R^1$ is chosen from $(C_1-C_7)$alkyl, benzyl, and —SO$_2$$(C_1-C_3)$alkyl.

7. A compound according to claim 6 wherein $R^1$ is —SO$_2$$(C_1-C_3)$alkyl.

8. A compound according to claim 5 wherein $R^1$ is $(C_1-C_7)$hydrocarbyl.

9. A compound according to claim 1 wherein the ring junction of the octahydro-1H-pyrano[3,4-b]pyrazine is trans and —NR$^5$R$^6$ is cis to its adjacent hydrogen at the ring junction.

10. A compound according to claim 1 wherein —NR$^5$R$^6$ is

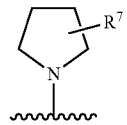

wherein $R^7$ is chosen from hydrogen, fluoro and $(C_1-C_3)$ alkyl.

11. A compound according to claim 1 wherein:
$R^1$ is chosen from hydrogen, $(C_1-C_7)$hydrocarbyl, —C(=O)O$(C_1-C_3)$hydrocarbyl and —SO$_2$$(C_1-C_8)$hydrocarbyl;
$R^2$, $R^3$, and $R^4$ are chosen independently from hydrogen, halogen, $(C_1-C_3)$alkyl, and fluoro$(C_1-C_3)$alkyl;
$R^5$ and $R^6$ are chosen from $(C_1-C_6)$hydrocarbyl, or, taken together with the nitrogen to which they are attached, $R^5$ and $R^6$ form a five-, six- or seven-membered non-aromatic heterocycle; and
$R^8$ is hydrogen.

12. A compound according to claim 11 wherein:
$R^1$ is chosen from hydrogen, $(C_3-C_4)$alkyl, —C(=O)O $(C_1-C_3)$hydrocarbyl, and —SO$_2$$(C_1-C_8)$hydrocarbyl;
$R^2$ is hydrogen;
$R^3$ and $R^4$ are chosen independently from hydrogen, halogen, $(C_1-C_3)$alkyl, and fluoro$(C_1-C_3)$alkyl; and
$R^5$ and $R^6$, taken together with the nitrogen to which they are attached, form a five-, six- or seven-membered non-aromatic heterocycle.

13. A compound according to claim 11 wherein:
$R^1$ is methyl or $(C_1-C_7)$hydrocarbyl.

14. A compound according to claim 11 wherein $R^1$ is —CH$_2$R$^{10}$ and $R^{10}$ is hydrogen or $(C_4-C_6)$carbocycle.

15. A compound according to claim 11 wherein $R^1$ is H, $R^5$ is methyl and $R^6$ is methyl or cyclopropylmethyl.

16. A compound according to claim 11 wherein:
$R^3$ is fluoro$(C_1-C_3)$alkyl when $R^2$ and $R^4$ are hydrogen.

17. A compound according to claim 11 wherein:
$R^5$ and $R^6$ together with nitrogen form a pyrrolidine ring.

18. A method for activating a kappa opioid receptor, comprising contacting a kappa opioid receptor with a compound according to claim 1.

19. A method for treating addiction, comprising administering to a patient a compound according to claim 1.

20. A method according to claim 19 wherein said addiction is an addiction to cocaine.

* * * * *